(12) United States Patent
Quirk et al.

(10) Patent No.: US 12,377,254 B2
(45) Date of Patent: Aug. 5, 2025

(54) TATTOO DEVICE

(71) Applicant: Active Needle Technology LTD, Abingdon (GB)

(72) Inventors: Ian Hugh Quirk, Oxford (GB); Muhammad Rohaan Sadiq, Aylesbury (GB); Andrea Giacomo Mica, Oxford (GB)

(73) Assignee: Active Needle Technology LTD, Abingdon (GB)

( * ) Notice: Subject to any disclaimer, the term of this patent is extended or adjusted under 35 U.S.C. 154(b) by 1000 days.

(21) Appl. No.: 17/290,493

(22) PCT Filed: Nov. 4, 2019

(86) PCT No.: PCT/GB2019/053119
§ 371 (c)(1),
(2) Date: Apr. 30, 2021

(87) PCT Pub. No.: WO2020/089658
PCT Pub. Date: May 7, 2020

(65) Prior Publication Data
US 2021/0370036 A1     Dec. 2, 2021

(30) Foreign Application Priority Data
Nov. 2, 2018   (GB) ...................................... 1817950

(51) Int. Cl.
*A61M 37/00*     (2006.01)
(52) U.S. Cl.
CPC .... *A61M 37/0076* (2013.01); *A61M 37/0092* (2013.01); *A61M 2205/0294* (2013.01);
(Continued)

(58) Field of Classification Search
CPC .............. A61M 37/00; A61M 37/0076; A61M 37/0092; A61M 2205/8275;
(Continued)

(56) References Cited

U.S. PATENT DOCUMENTS

2002/0169394 A1\* 11/2002 Eppstein ............ A61B 5/15136
600/573
2010/0192730 A1   8/2010 Dubin
(Continued)

FOREIGN PATENT DOCUMENTS

CN           2517389        10/2002
DE        102008031907       1/2010
(Continued)

*Primary Examiner* — Vi X Nguyen
(74) *Attorney, Agent, or Firm* — Jordan IP Law, LLC

(57) ABSTRACT

A tattoo device is provided comprising a housing having a first oscillator which is coupled, in use, to a needle assembly having a sharps end. The first oscillator is arranged and adapted to induce vibrations at a frequency from 1-1000 Hz substantially longitudinally along an axis of the needle assembly in order to cause, in use, the sharps end to penetrate skin. The tattoo device further comprises a second oscillator which is also coupled, in use, to the needle assembly, wherein the second oscillator is arranged and adapted simultaneously to induce vibrations at a higher frequency than the first oscillator and in particular at a frequency from 5-200 kHz in order to lower the insertion force required to penetrate skin layers.

18 Claims, 19 Drawing Sheets

(52) U.S. Cl.
CPC ................ *A61M 2205/106* (2013.01); *A61M 2205/8275* (2013.01)

(58) Field of Classification Search
CPC .... A61M 2205/106; A61M 2205/0294; A61B 17/205; A61B 17/00491
See application file for complete search history.

(56) References Cited

U.S. PATENT DOCUMENTS

| | | | | |
|---|---|---|---|---|
| 2012/0209303 | A1* | 8/2012 | Frankhouser | A61M 5/3287 606/169 |
| 2012/0265232 | A1 | 10/2012 | Surbone | |
| 2014/0271897 | A1* | 9/2014 | Pathak | A61K 31/496 514/254.11 |
| 2017/0354810 | A1 | 12/2017 | O'Brien, III | |
| 2018/0000419 | A1* | 1/2018 | Rassman | A61B 5/01 |

FOREIGN PATENT DOCUMENTS

| | | |
|---|---|---|
| JP | H09239031 | 9/1997 |
| JP | 2007-533623 | 11/2007 |
| KR | 101181974 | 9/2012 |
| KR | 10-1692983 | 1/2017 |
| WO | 2018/170176 | 9/2018 |

* cited by examiner

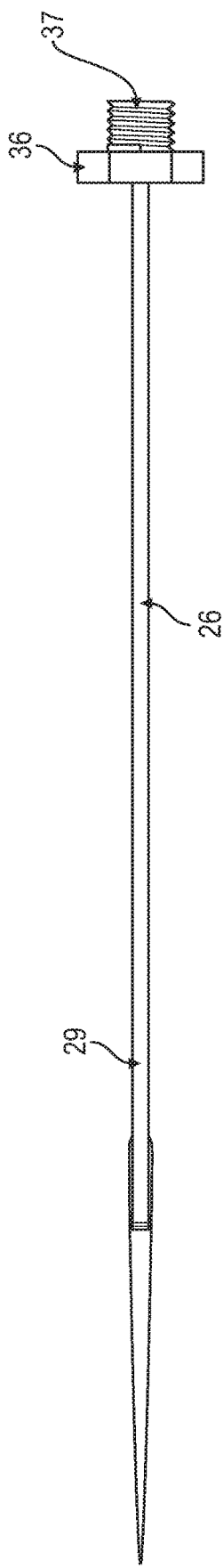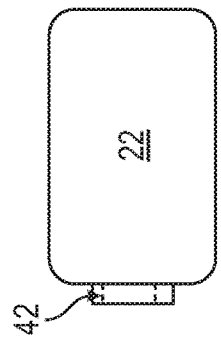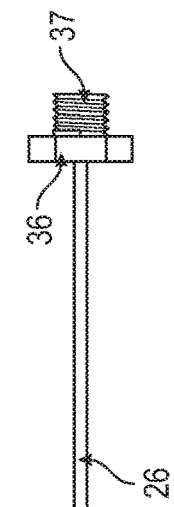
FIG. 9
FIG. 10

TATTOO DEVICE

CROSS-REFERENCE TO RELATED APPLICATION APPLICATIONS

This application represents the U.S. National Phase of International Application number PCT/GB2019/053119 entitled "Tattoo Device" filed 4 Nov. 2019, which claims priority from and the benefit of United Kingdom patent application No. 1817950.7 filed on 2 Nov. 2018. The entire contents of these applications are incorporated herein by reference.

FIELD OF THE INVENTION

The present invention relates to a tattoo device, a method of applying a tattoo to a human or an animal and a tattoo needle. Various embodiments relate to a vibrating needle and in particular to a vibrating tattoo needle assembly for use in tattooing devices.

BACKGROUND TO THE PRESENT INVENTION

Tattooing devices for performing cosmetic tattoos on humans and also on animals are well known. Various different types of tattoo devices are known.

A first type of tattoo device comprises a pair of electromagnetic coils which are arranged to move an armature bar up and down. A needle grouping is connected to the armature bar. The vibrating needle grouping is arranged to push ink into the skin of a subject.

A second type of tattoo device comprises a rotary tattoo device which comprises a DC electric motor which is connected to a cam with a protruding nipple offset from a central axis of the motor housing. One end of the needle assembly is mounted to the nipple by means of an end loop. The needle assembly is moved backwards and forwards along the central longitudinal axis of the needle assembly by the rotational movement of the cam thereby providing the desired tattooing motion.

A third less common type of tattoo device comprises a pneumatically driven tattoo device. Pneumatically powered tattoo devices utilise compressed air to drive a cam which rotates. The cam provides an offset nipple and a needle assembly is attached thereto.

Current tattooing methods involve piercing the skin using a needle which vibrates in a longitudinal manner allowing ink to enter the dermis. Ink enters the dermis where the ink is retained thus forming the desired pattern or mark. The user may control the speed at which the longitudinal vibration of the needle occurs by varying the power supplied to the tattoo device. The tattoo device typically operates at a frequency in the range from 120-150 Hz for lining operations and 80 Hz for shading operations.

US 2018/0000419 (Rassman) discloses a tattooing device having one or more sensors for dynamically sensing changes in skin characteristics as the needle(s) penetrate the skin of the scalp. The tattoo device is capable of reducing the exposure of tattoo artists to repetitive stress disorders. In particular, the needle movement may be halted upon completion of a spot which minimises the duty cycle of operation thereby reducing the operator's time of exposure to 50-150 Hz vibrations which are most commonly cited as a cause of hand-arm-vibration syndrome ("HAVS"). According to an arrangement destructive mechanical or acoustic interference may be provided to further reduce vibration exposure. According to an arrangement a vibrating element such as a piezoelectric crystal or small motor may be provided to provide vibrations to generate destructive interference for the primary mechanical vibration.

Conventional methods of tattoo application can cause pain to the subject as the needle or needles impact the skin. Both the initial impact of the needle to the skin and the proceeding motion can cause varying levels of pain to the subject and may subsequently cause bleeding and scabbing which is undesirable when applying a tattoo. The frequent penetration of the needle can also provoke an immune response and a resultant feeling akin to a minor illness in the subject. This response can persist for hours or days.

It is desirable to provide an improved tattoo device which causes substantially less pain and/or skin trauma to the subject whilst being tattooed.

SUMMARY OF THE PRESENT INVENTION

According to an aspect of the present invention there is provided a tattoo device comprising:
a housing;
a first oscillator which is coupled, in use, to a needle having a sharps end, wherein the first oscillator is arranged and adapted to induce vibrations at a frequency from 1-1000 Hz substantially longitudinally along an axis of the needle in order to cause, in use, the sharps end to penetrate skin; and
a second oscillator which is coupled, in use, to the needle;
wherein the second oscillator is arranged and adapted to induce vibrations at a higher frequency than the first oscillator and at a frequency from 5-200 kHz in order to lower the insertion force required to penetrate skin layers.

According to various embodiments a tattoo device is provided comprising a housing and a tattoo needle assembly attached thereto. In addition to conventional lengthwise tattooing motion at a base frequency of, for example, 1-1000 Hz or 1-500 Hz which controls the entry and exit of the needle into the skin, the needle assembly is additionally vibrated at a second comparatively higher frequency.

According to various preferred embodiments the tattoo device comprises a second oscillator which is also coupled to the needle assembly and which additionally and simultaneously vibrates the needle assembly at a second higher frequency which may be in the range 1-200 kHz or 5-200 kHz. The second higher frequency of vibration which provides needle vibration in addition to lengthwise vibrations of the base frequency advantageously lowers both the insertion forces of the needle and the resulting forces experienced by the skin. As a result, a tattooing device according to various embodiments of the present invention results in a considerable reduction in the sensation of pain as experienced by the subject being tattooed.

It will be appreciated, therefore, that a tattoo device according to the present invention represents a significant advance in the art.

The arrangement disclosed in US 2018/0000419 (Rassman) is not relevant to the present invention. According to the arrangement disclosed in US 2018/0000419 (Rassman) the needle is vibrated at a frequency of 50-150 Hz. A second vibrating element such as a piezoelectric crystal or small motor may be provided to provide vibrations to generate destructive interference for the primary mechanical vibration. Accordingly, it will be understood that the second vibrating element also vibrates at the same frequency as the primary drive frequency i.e. at a frequency 50-150 Hz but that the second vibrating element is arranged to vibrate in anti-phase to the primary drive frequency. As a result, the two vibration sources result in destructive interference such that needle effectively ceases to vibrate thereby stopping a tattoo artist from experiencing vibrations when the device is not in use. It will be understood that prolonged exposure to vibrations over a substantial period of time is potentially harmful and hence the arrangement disclosed in US 2018/0000419 (Rassman) helps to reduce vibration exposure.

It will be understood that US 2018/0000419 (Rassman) does not therefore disclose providing a second oscillator which is arranged and adapted to induce vibrations at a higher frequency than a first (primary drive) oscillator. In particular, US 2018/0000419 (Rassman) does not disclose providing and operating a second oscillator at a frequency in the range 5-200 kHz in order to lower the insertion force required to penetrate skin layers.

According to embodiments of the present invention the needle assembly may comprise a longitudinal needle body having a first sharps end which may comprise a single point or an array of points. It is known in tattooing that different needle arrays may be used to create different effects. For example, line, shading and colouring may be achieved by different patterns and quantities of needle points, all branching from the same needle stem.

The tattoo device may be configured to connect to a needle or needle assembly at a distance from the sharps end.

The tattoo device comprises a first and second oscillator which are coupled, in use, to the needle or needle assembly such that energy may be efficiently transferred thereto so as to oscillate the needle or needle assembly and the sharps end thereof.

The first and/or second oscillators may be contained in the housing of the tattoo device. Alternatively, one or both of the oscillators may be attached to the needle or needle assembly outside the housing. According to an embodiment one or both of the oscillators may be integral with the needle or needle assembly.

The second oscillator preferably comprises a transducer and may comprise a piezo electric device.

The needle or needle assembly may be releasably connected to the tattoo device thereby permitting the interchange of needles for reasons of hygiene or to change needle type during a tattoo procedure. The connection between the needle or needle assembly and the tattoo device may comprise a male connection member and a corresponding female connection member which may be configured to mate with each other.

According to an embodiment the male connection member may be provided on the needle or needle assembly and the female connection member may be provided on the remainder of the tattoo device. According to an alternative embodiment, the female connection member may be provided on the needle or needle assembly and the male connection member may be provided on the remainder of the tattoo device.

The connection arrangement may comprise a screw mechanism. A screw mechanism may provide a large point of contact between the needle or needle assembly and a transducer thereby helping to ensure that there is a secure and stable connection between the needle or needle assembly and the transducer. A larger point of contact may also provide more reliable transmission of vibrations from the transducer to the needle or needle assembly. As a result, there may be less energy loss, making the connection more efficient in terms of energy transfer.

Alternatively, the connection arrangement may comprise a bayonet mechanism. The connection arrangement may comprise a snap-fit mechanism. Both a bayonet and snap-fit connection mechanism may provide a large, secure point of contact between the needle or needle assembly and remainder of the tattoo device. A bayonet or snap-fit connection does not rely on the provision of compression or a gripping mechanism in order to secure the needle or needle assembly to the transducer or more generally to a headpiece which may house the transducer.

The needle or needle assembly may be connected to the remainder of the tattoo device using a connection member. The connection member may be connected between the needle or needle assembly and the remainder of the tattoo device. The connection member may comprise an additional intermediate component between the needle or needle assembly and the remainder of the tattoo device. The additional intermediate component may comprise a floating free mass to increase vibration amplitude. The needle or needle assembly may be connected to the connection member using a screw mechanism. The needle or needle assembly may be connected to the connection member using a bayonet mechanism. The needle or needle assembly may be connected to the connection member using a snap-fit mechanism. The needle or needle assembly may be connected to the connection member using a clip mechanism. The transducer may be connected to the connection member using any of the aforementioned connection means. The needle or needle assembly and the transducer may be connected to the connection member using the same or different connection means.

The connection member may comprise a clip. The clip may comprise a first and a second gripping end. The first gripping end may be configured for attachment to the needle or needle assembly. The second gripping end may be configured for attachment to the remainder of the tattoo device. The first and second gripping ends may comprise first and second arms. The first and second arms may be curved. The clip may be made of plastic.

The provision of an intermediate connection member may allow the needle or needle assembly and transducer to be connected together without the need to redesign either the needle or needle assembly or the transducer to allow the connection to happen. Thus conventional needles or needle assemblies may be connected to the tattoo device of the present invention. The tattoo device may be configured to vibrate conventional needles or needle assemblies through the use of the connection member such that a specially designed needle or needle assembly does not need to be used.

The tattoo device according to the present invention comprises a first and a second oscillator which are operably coupled to the needle or needle assembly.

The first oscillator is preferably adapted to produce vibrations at relatively low frequencies, such as from 1 to 1000 Hz, preferably 5 to 250 Hz, more preferably from 10 to 150 Hz. Embodiments are contemplated wherein the first oscillator may oscillate or produce vibrations at a frequency 1 kHz. The first oscillator may comprise a known oscillator such as: (i) an electromagnetic coil which utilises electric current which passes through the electromagnetic coil, a pair of coils or a multiplicity of coils to provide oscillation; (ii) a rotary oscillator which utilises an eccentric attachment to the spindle of an electric motor; or (iii) a pneumatic oscillator which utilises compressed air to force a motor to spin which in turn is arranged to crank a needle bar up and down.

The first oscillator may also comprise an oscillator which utilises a fluid to drive the oscillator.

The magnitude of the oscillations produced by the first oscillator may be between 0.1 and 10 mm, preferably between 1 and 6 mm.

The first oscillator is preferably operably coupled to the needle or needle assembly in order to induce vibrations substantially longitudinally along the axis of the needle or needle assembly. The first oscillator preferably produces oscillations of a frequency and magnitude which is preferably sufficient to cause the sharps end of the needle or needle assembly to penetrate the dermis and cause a puncture into which the tattoo ink is subsequently introduced.

The tattoo device preferably further comprises a second oscillator. The second oscillator is preferably configured to produce vibrations at a second higher frequency than the first oscillator. The second oscillator may be configured to produce oscillations or vibrations at between 5 kHz and 200 kHz, preferably between 10 kHz and 100 kHz, more preferably between 25 kHz and 75 kHz such as around 40 kHz.

The magnitude of the oscillations or vibrations produced by the second oscillator is preferably smaller than those produced by the first oscillator. The oscillations produced by the second oscillator are preferably between 0.1 and 500 µm, more preferably between 1 and 100 µm.

Surprisingly, it has been found that this high frequency motion has the effect of lowering the insertion forces required to penetrate the skin layers with the result of reducing pain (nociception) and other triggers. In addition, pain can be triggered after insertion but before removal in a stroke of the needle or needle assembly by dint of the friction caused by the moving needle or needle assembly. The high frequency motion of the needle or needle assembly greatly reduces these frictional forces, further reducing pain and skin trauma triggers.

The second oscillator may comprise an electromagnetic coil which is coupled to the needle or needle assembly. The electromagnetic coil may be arranged so that the electromagnetic coil surrounds the needle or needle assembly about a longitudinal axis of the needle or needle assembly. The electromagnetic coil may be arranged so that the electromagnetic coil vibrates the needle or needle assembly by attachment to any section of the needle or needle assembly. In this configuration, the second oscillator is indirectly coupled to the needle or needle assembly. The second oscillator may comprise a pulsatory material which is preferably suitably coupled to the needle or needle assembly. The pulsatory material may comprise a piezo-electric material such as a ceramic, crystal or other material such that an oscillatory response is provided from a stimulus. The stimulus may be provided by an electric current, such as an alternating current. The electricity for the stimulus may be provided via a transducer. A plurality of pulsatory materials may be coupled to the needle or needle assembly and may be arranged to provide symmetry and an even weight distribution across the needle arrangement.

The second oscillator may be configured to attach to an armature bar of a tattoo device. The second oscillator may be connected to the armature bar by way of a connection arrangement.

The second oscillator may comprise a second end which is configured to attach to a modified armature bar of a tattoo device. The armature bar may be modified to connect to the second oscillator using a screw mechanism. The armature bar may be modified to connect to the second oscillator using a bayonet mechanism. The armature bar may be modified to connect to the second oscillator using a snap-fit mechanism. The armature bar may be modified to connect to the second oscillator using a clip mechanism. The second oscillator may be connected to the connection member using any of the aforementioned connection means.

The armature bar may be modified to provide a socket to which the second oscillator is connected. The socket may be threaded so as to receive a corresponding threaded second oscillator collar. The socket may be smooth to allow a corresponding second oscillator bolt to be inserted. The armature bar may have a hole in which a second oscillator bolt may be inserted. The socket may be partly threaded. The second oscillator bolt may be threaded at its proximal end to engage with a nut. The second oscillator bolt may be partly threaded. The nut may be tightened against the armature bar to mount the second oscillator and needle arrangement to the tattoo device.

The second oscillator may comprise a connector which is configured to attach to a modified cam of a tattoo device. The cam may be attached to a motor. The cam may provide an offset protruding connection means, such as a nipple. The cam may be modified to connect to the second oscillator using a screw mechanism. The cam may be modified to connect to the second oscillator using a bayonet mechanism. The cam may be modified to connect to the second oscillator using a snap-fit mechanism. The cam may be modified to connect to the second oscillator using a clip mechanism. The second oscillator may be connected to the cam using any of the aforementioned connection means.

The cam may be modified to provide a socket to which the second oscillator is connected. The socket may be threaded so as to receive a corresponding threaded second oscillator collar. The socket may be smooth to allow a corresponding second oscillator bolt to be inserted. The cam may have a hole in which a second oscillator bolt may be inserted. The socket may be partly threaded. The second oscillator bolt may be threaded at its proximal end to engage with a nut. The second oscillator bolt may be partly threaded. The nut may be tightened against the cam to mount the second oscillator and needle arrangement to the tattoo device.

The amplitude and/or frequency of the voltage supplied to the second oscillator may be manually controlled by a user. The user may control the voltage and/or frequency using a control panel. This may allow the user to adjust the voltage and/or frequency so that it is optimised for different types of needle. Thus, the user may ensure that the needle or needle assembly being used is being vibrated at its optimum frequency for tattooing.

The amplitude and/or frequency of the voltage supplied to the second oscillator may be controlled by an electronic control programme which may be programmed so as to maintain the required frequency of oscillation. The programme may receive feedback from the needle or needle assembly and may interpret the data to vary the amplitude and/or frequency and subsequently maintain the required levels of needle oscillation.

The needle or needle assembly may be housed in a needle housing. The needle housing may comprise a grippable section for controlling the position and movement of the tattoo device when in use. The grippable section may be ergonomically designed to fit the human hand. The grippable section may provide a surface which increases friction between the grippable section and the human hand. The grippable section may comprise an arrangement of ribs to aid the gripping of the tattoo device.

The tattoo device preferably further comprises a reciprocating device which is arranged and adapted to permit the second oscillator to slide or reciprocate within the housing of the tattoo device. The reciprocating device preferably comprises one or more guide rails, one or more linear slides or one or more linear motion bearings. Advantageously, the reciprocating device enables the second oscillator to move, slide or reciprocate relative to the housing which may comprise a handpiece.

According to an aspect of the present invention there is provided a tattoo device comprising a housing, a needle, a first oscillator and a second oscillator, wherein the first and second oscillator are coupled to the needle to induce vibrations therein, wherein the first and second oscillators operate at different frequencies.

The first oscillator preferably operates at a frequency of from 1 to 1000 Hz, preferably 1-500 Hz, further preferably 5 to 250 Hz, more preferably from 10 to 150 Hz.

The first oscillator is preferably selected from a coil or pair of coils; a rotary oscillator; and a pneumatic oscillator.

According to various embodiments the second oscillator operates at a frequency of between 1 kHz to 200 kHz, preferably 5 kHz and 200 kHz, further preferably between 10 kHz and 100 kHz, more preferably between 25 kHz and 75 kHz such as around 40 kHz.

The tattoo device is preferably arranged and adapted to reduce the subject's perception of pain.

The second oscillator preferably comprises a magnetic coil in communication with the needle.

The second oscillator may comprise a piezoelectric oscillator.

The piezoelectric oscillator may be in the form of a single crystal coupled to the needle.

The piezoelectric oscillator may be in the form of two or more crystals coupled to the needle.

The piezoelectric oscillator may also comprise one or more ceramic oscillators. For example, the one or more ceramic oscillators may comprise lead zirconate titanate ("PZT").

The tattoo device may further comprise: (i) a horn configured to amplify the oscillations of the second oscillator; and/or (ii) a floating mass located within a chamber positioned between the second oscillator and a needle or needle assembly.

According to an embodiment one or both oscillators may be adapted to oscillate at a frequency controlled by an operator.

According to various embodiments there is provided a needle adapted to be used in a tattoo device as described above.

According to another aspect of the present invention there is provided a use of a piezoelectric oscillator to vibrate the needle of a tattoo device at a second frequency higher than the normal operating frequency of the device.

According to another aspect of the present invention there is provided a method of applying a tattoo to a human or an animal comprising:
(i) providing a needle having a sharps end;
(ii) vibrating the needle simultaneously at a frequency of from 1 to 1000 Hz and a second frequency of from 5 kHz and 200 kHz;
(iii) bringing the sharps end of the needle into contact with the skin of a human or animal so as to cause punctures therein; and
(iv) applying ink to the punctures.

The method of applying a tattoo to a human or an animal preferably comprises either a non-therapeutic method. According to the preferred embodiment the method of applying a tattoo to a human or an animal preferably comprises a non-surgical method. The method of applying a tattoo to a human or an animal preferably comprises a cosmetic method.

The tattoo is preferably cosmetic and may comprise a mark of identification.

According to other embodiments the method may be utilised as a method of surgical reconstruction. Various embodiments of the present invention are contemplated which relate to a therapeutic or surgical method.

According to another aspect of the present invention there is provided a method of surgical reconstruction comprising:
(i) providing a needle having a sharps end;
(ii) vibrating the needle simultaneously at a frequency of from 1 to 1000 Hz and a second frequency of from 1 kHz and 200 kHz; and
(iii) bringing the sharps end of the needle into contact with the skin of a human or animal so as to cause punctures therein.

Optionally, the method may further comprise the step of (iv) applying ink or another chemical or biological substance to the punctures. For example, it may be desired to apply a drug, biochemical substance or therapeutic substance at a surface level of the skin or in the dermis of a patient.

According to an embodiment the method may be used for vitiligo correction. Vitiligo is a long-term condition where pale white patches develop on the skin. It is caused by the lack of melanin, a pigment in the skin. Melanin is produced by skin cells called melanocytes and it is responsible for giving skin its colour. It will be appreciated that the pale white patches can cause distress to a sufferer especially if they are present on a visible area of the body such as the face or the hands. Accordingly, methods are contemplated wherein blemishes in skin tone may be permanently or semi-permanently corrected for.

According to another aspect of the present invention there is provided a method of treating vitiligo, melanin deficiency or skin tone blemishes comprising:
(i) providing a needle having a sharps end;
(ii) vibrating the needle simultaneously at a frequency of from 1 to 1000 Hz and a second frequency of from 1 kHz and 200 kHz;
(iii) bringing the sharps end of the needle into contact with the skin of a human or animal so as to cause punctures therein; and
(iv) applying ink or another chemical or biological substance to the punctures.

The method may comprise a therapeutic or non-therapeutic method.

According to another aspect there is provided a substantially symmetric tattoo needle for use in conjunction with a tattoo device as described above.

BRIEF DESCRIPTION OF THE DRAWINGS

Various embodiments of the present invention together with other arrangements given for illustrative purposes only will now be described, by way of example only, and with reference to the accompanying drawings in which:

FIG. 9 shows a side view of a needle assembly according to a preferred embodiment with a singularly pointed needle end and transducer attachment means;

FIG. 10 shows a side view of a needle assembly according to a preferred embodiment with a singularly pointed needle end, transducer attachment means and a disconnected transducer unit;

DETAILED DESCRIPTION

Various different types of tattoo device are known. In particular, known tattoo devices comprise a needle assembly which is vibrated either by a couple of electromagnetic coils in conjunction with an armature or by a DC electric motor which rotates a cam.

Figure 1:
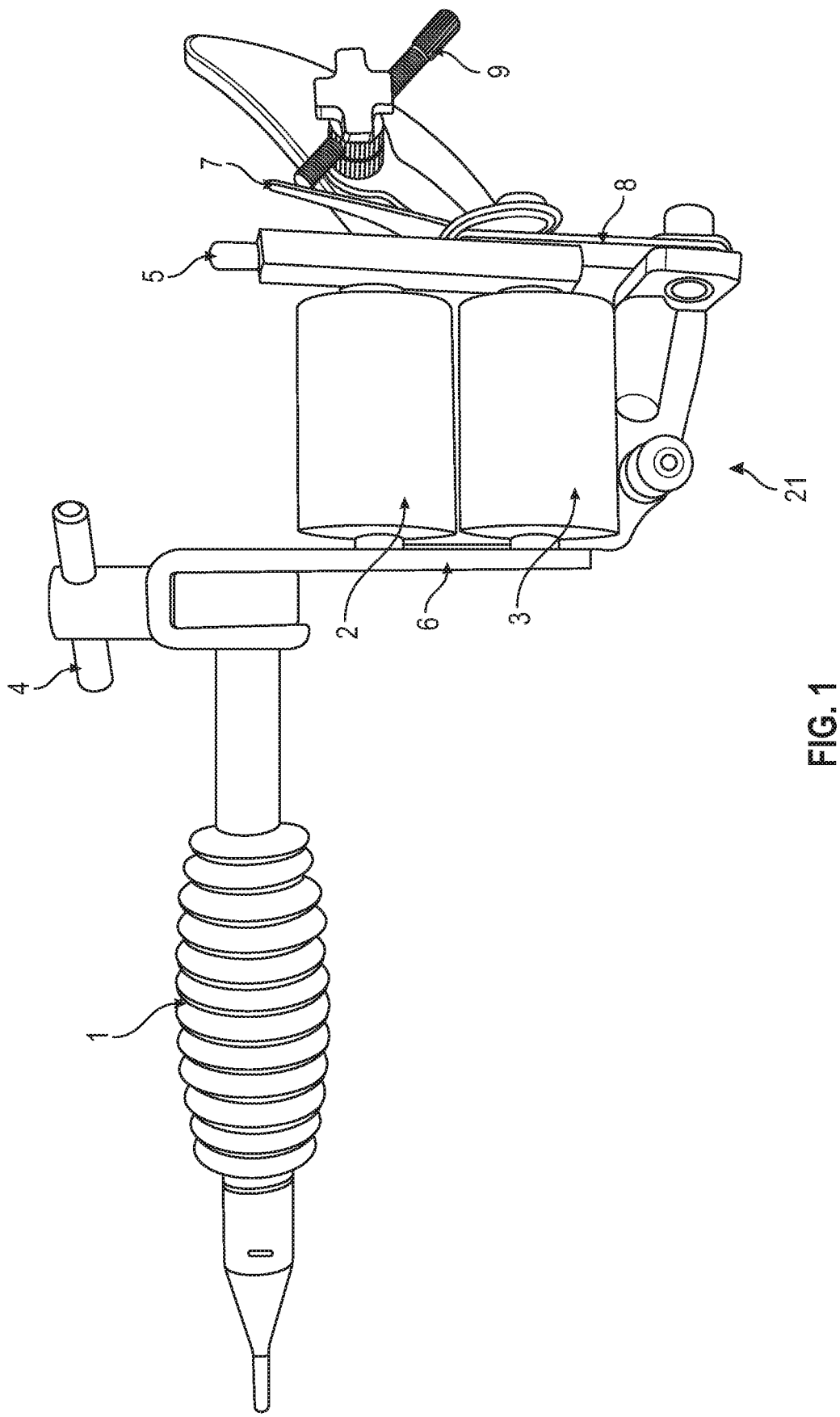
FIG. 1 shows a known tattoo device comprising a pair of electromagnetic coils which are arranged to vibrate a needle assembly.

FIG. 1 shows a known electromagnetic coil tattoo device. The known electromagnetic coil tattoo device comprises a tattoo device body 21 having a frame base 6 which supports a drive mechanism comprising a front coil 2 and a back or rear coil 3 in conjunction with a motive armature 5. A needle assembly is connected to the drive mechanism via a tube vise (or vice) thumbscrew 4. A user grip 1 is provided which surrounds the needle assembly. The tattoo device further comprises a front spring 7, a back spring 8 and a contact screw 9.

Figure 2:
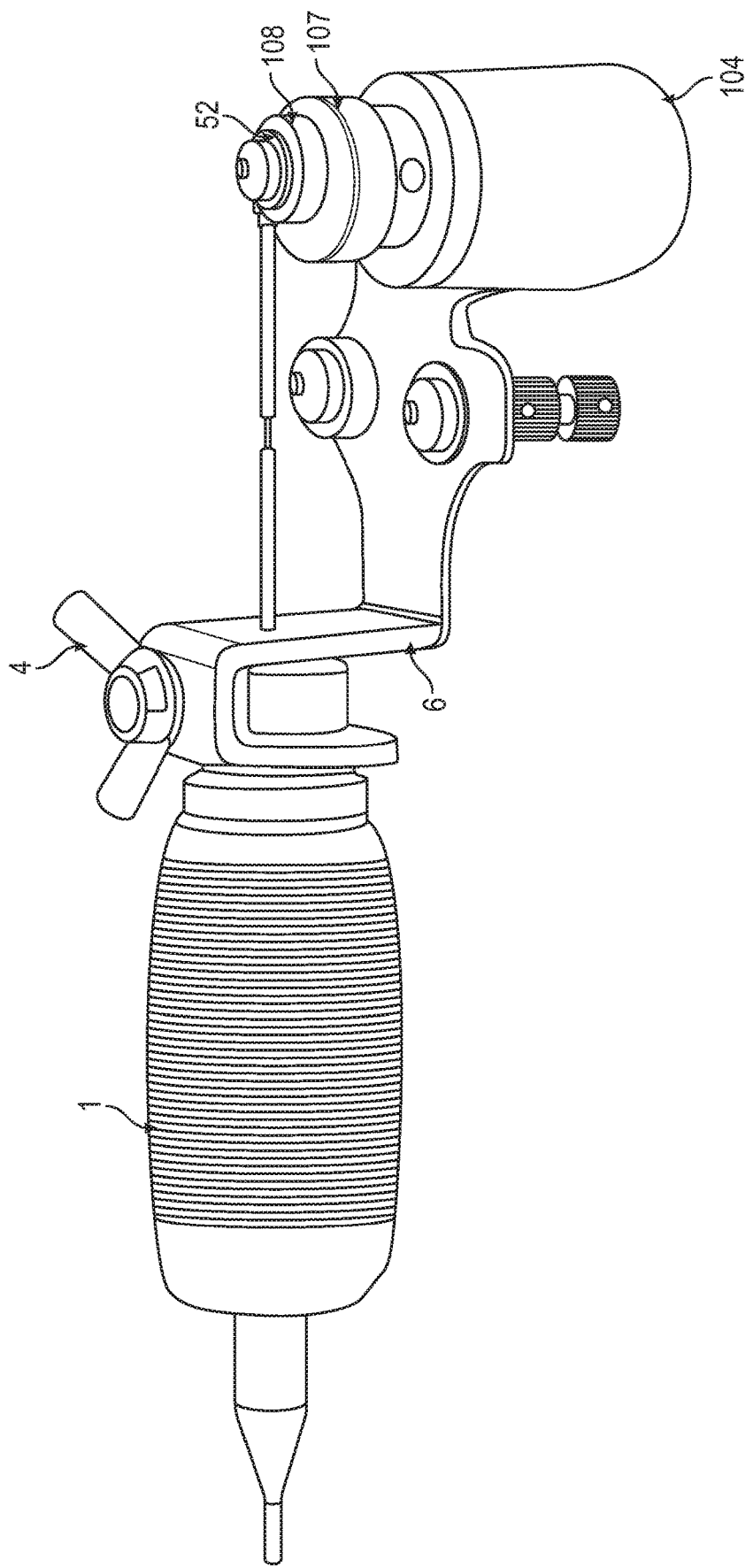
FIG. 2 shows another known tattoo device having a rotary drive mechanism wherein a DC electric motor is arranged to rotate a cam having a protruding nipple to which a loop end of a needle assembly is attached.

FIG. 2 shows a known rotary tattoo device. The known rotary tattoo device comprises a frame base 6 which supports a motor housing. The motor housing houses a DC electric motor 104 which is connected to a cam 107 having a protruding nipple 108. The protruding nipple 108 is offset from the central axis of the motor housing. A needle assembly having a sharps end at one end and an end loop 52 at the other end is connected or otherwise mounted to the nipple 108 via the end loop 52. The needle assembly passes through a tube vise (or vice) thumbscrew 4 which supports a user grip 1. The needle assembly will vibrate backwards and forwards along the longitudinal central axis of the needle assembly by the rotational movement of the cam 107 thereby providing the desired tattooing motion.

A less common tattoo device comprises a pneumatically powered tattoo device.

Figure 3:
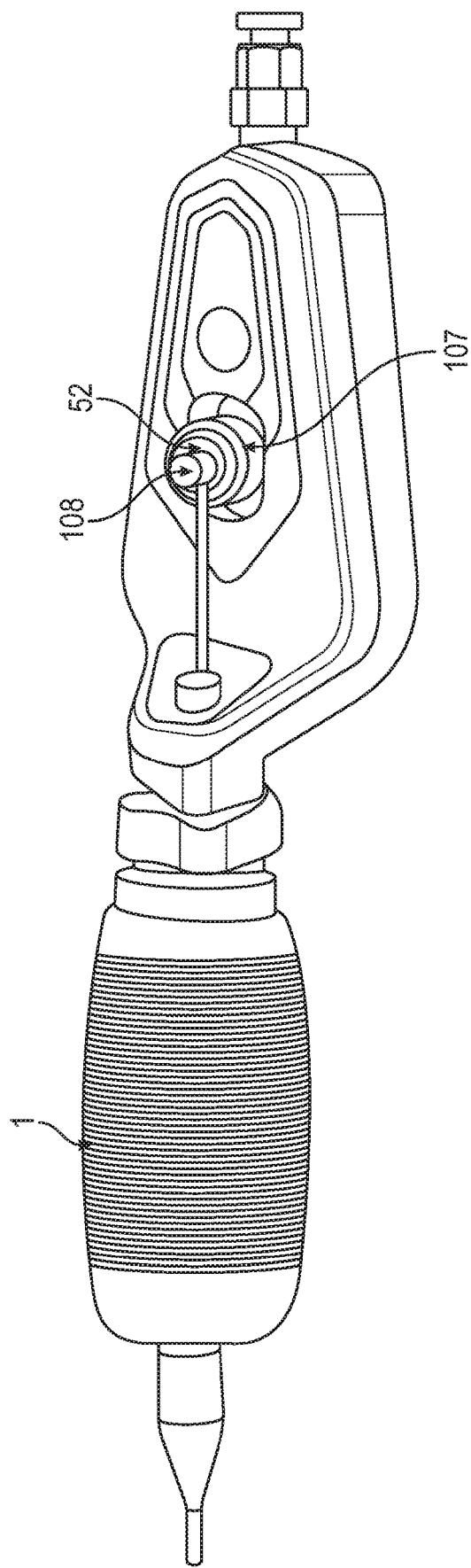
FIG. 3 shows another known tattoo device having a pneumatic drive mechanism wherein a cam is driven pneumatically so as to cause a needle assembly to vibrate.

FIG. 3 shows a known pneumatically powered tattoo device wherein compressed air is used to drive a cam 107 which has a protruding nipple 108. The cam 107 supports an offset nipple 108 and a loop end 52 of a needle assembly is attached to the protruding nipple 108. As the cam 107 rotates, the needle assembly is driven in a linear direction backwards and forwards along the central axis of the needle assembly. A user grip 1 surrounds the needle assembly.

Various embodiments of the present invention will now be described.

Figure 4:
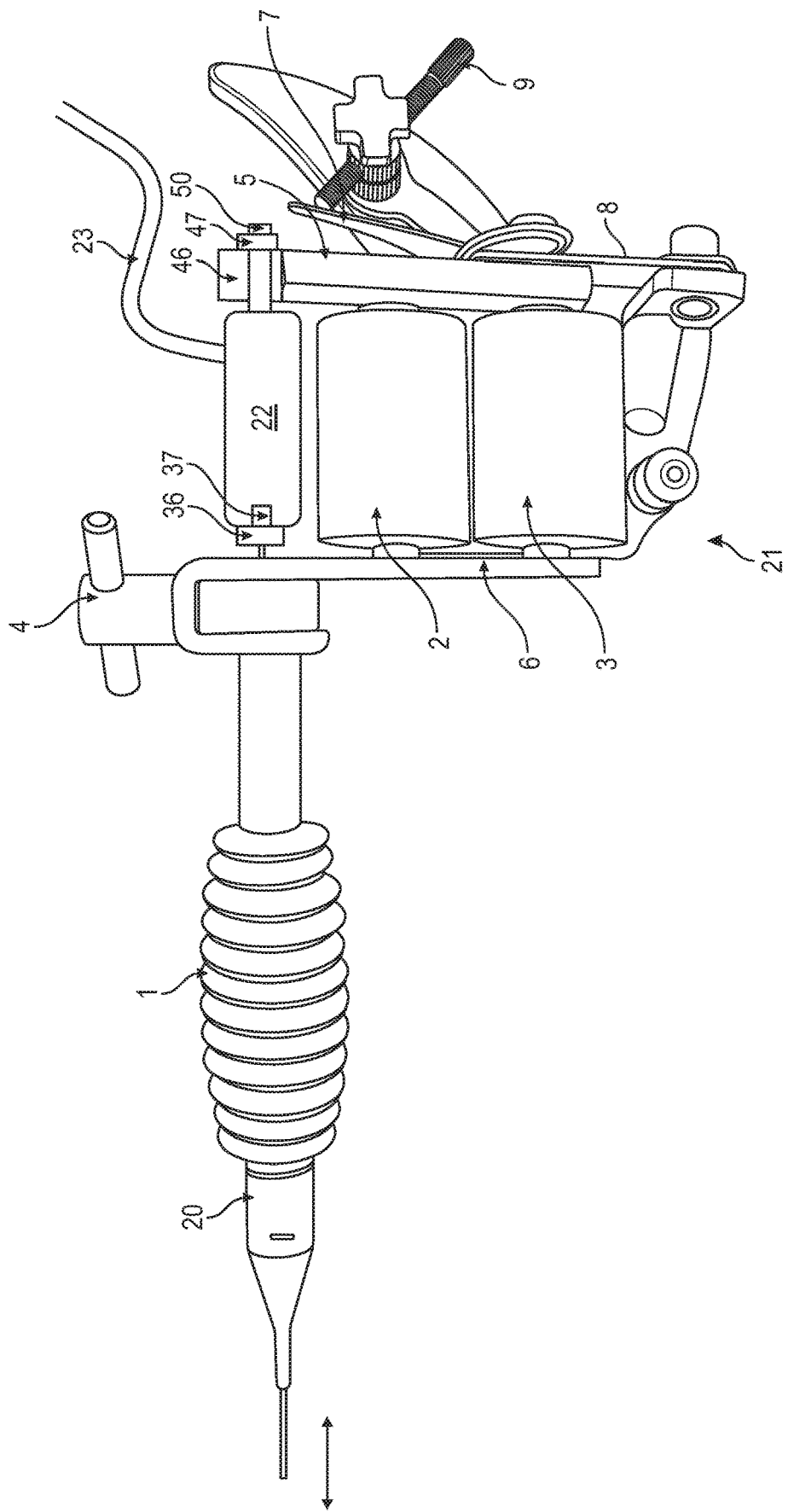
FIG. 4 shows a preferred embodiment of the present invention wherein a needle assembly is vibrated at a first drive frequency by a pair of electromagnetic coils and wherein in addition the needle assembly is additionally simultaneously vibrated by a transducer at a second higher frequency in order to reduce the insertion force required to penetrate layers of skin thereby reducing the pain sensation felt by a subject being tattooed.

FIG. 4 shows a preferred embodiment of the present invention wherein a vibrating needle assembly is connected to the body 21 of an electromagnetic coil tattoo device.

The electromagnetic coil tattoo device comprises a tattoo device body 21 having a frame base 6 which supports a drive mechanism comprising a front coil 2 and a back or rear coil 3 in conjunction with a motive armature 5. A needle assembly is connected to the drive mechanism via a tube vise (or vice) thumbscrew 4. A user grip 1 is provided which surrounds the needle assembly. The tattoo device further comprises a front spring 7, a back spring 8 and a contact screw 9.

According to this particular embodiment the tattoo device uses an electromagnetic coil system to generate low-frequency needle movement preferably at a first frequency of 1-1000 H or 1-500 Hz. According to various embodiments the first frequency may be 1 kHz.

The needle assembly is preferably housed in a needle housing 20 which is connected to the tattoo device body 21 via a transducer housed in a transducer housing 22. A transducer connecting wire 23 is shown which preferably connects to a user-controlled generator unit (not shown). The transducer 22 is preferably configured to provide high-frequency vibration to the needle or needle assembly preferably at a frequency of 1-200 kHz or 5-200 kHz. The frequency of the vibration may be controlled by the user by adjusting a controllable generator unit.

The electromagnetic coil system is preferably powered by a separate power supply which is also preferably controllable by the user in order to vary the frequency of the lengthwise needle vibration. The needle vibration may be activated by a user-actuated foot pedal.

The needle assembly is preferably connected to the transducer 22 via an end section of the needle assembly which preferably comprises a hexagonally profiled collar 36 having a protruding threaded cylinder 37 extending therefrom. The threaded cylinder 37 may be arranged such that it may be inserted into a corresponding female threaded socket provided in the transducer housing 22.

The armature bar 5 preferably has a hole provided at its distal end with a greater diameter than that of a transducer connecting bar 46. One end of the transducer connecting bar may have a threaded portion 47 which passes through the hole in the armature bar 5. This provides a protruding transducer bar end section to which a nut 50 may be screwed. By screwing the nut 50 against the threaded transducer bar section 47 in the direction of the transducer housing 22, the armature bar 5 is preferably connected to the transducer housing 22 and consequently, the needle assembly. As the assembly is completed, when armature bar movement is generated by the electromagnetic coil drive mechanism the needle will subsequently move in the required longitudinal direction for tattooing.

Figure 5:
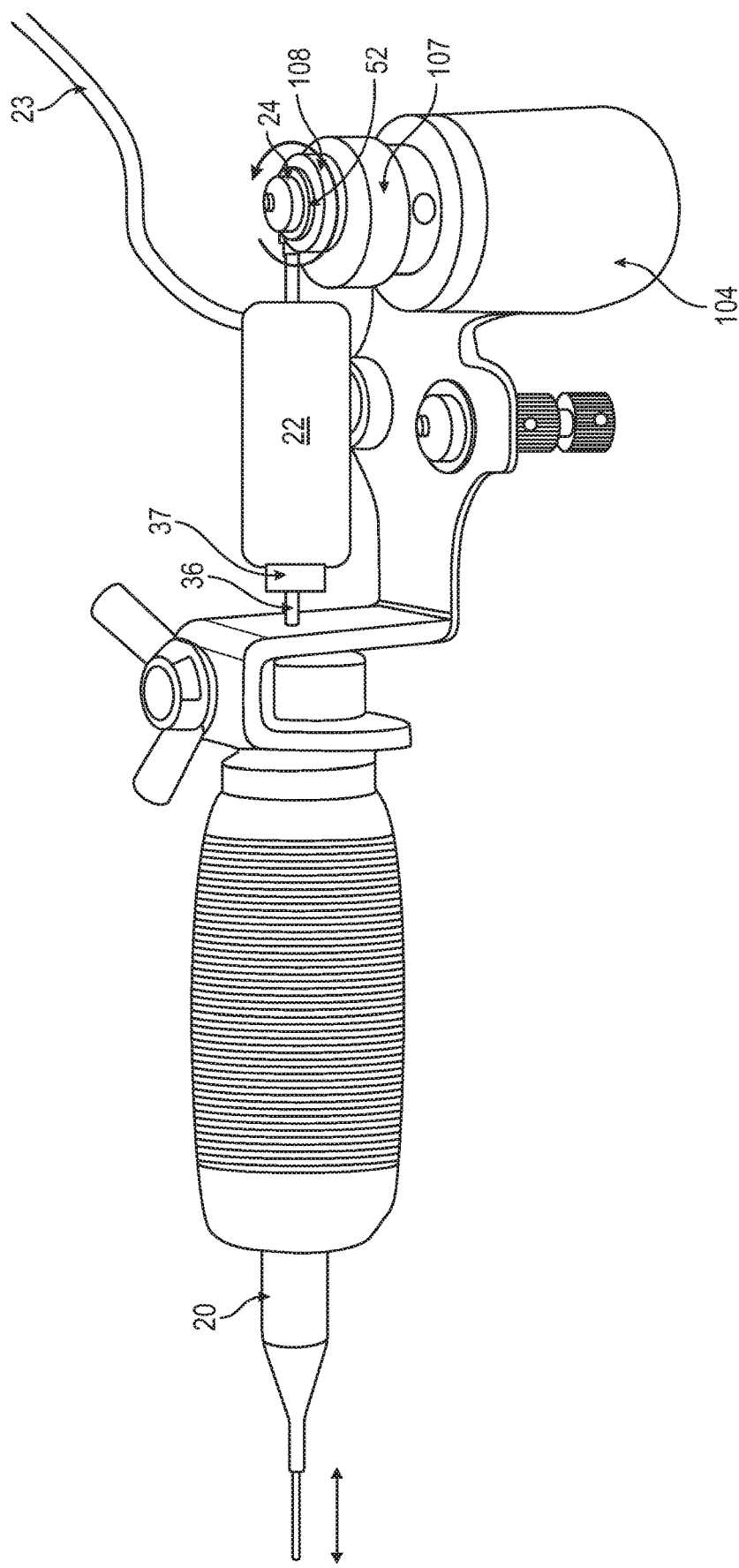
FIG. 5 shows another preferred embodiment of the present invention wherein a needle assembly is connected to a rotary drive mechanism and wherein the needle assembly is additionally simultaneously vibrated by a transducer at a second higher frequency in order to reduce the insertion force required to penetrate layers of skin thereby reducing the pain sensation felt by a subject being tattooed.

FIG. 5 shows another embodiment of the present invention wherein a rotary drive system is used to vibrate the needle assembly. According to this embodiment the needle assembly is attached to a rotary drive system via a transducer housing 22. One end of the needle assembly comprises a hexagonal profiled collar 36 having a protruding threaded cylinder 37 which is inserted into a corresponding female threaded socket in the transducer housing 38. The other end of the transducer comprises looped needle end 24 which attaches to a protruding nipple 108 provided on the surface of a cam 107. The cam 107 is preferably rotated by a DC electric motor 104.

Figure 6:
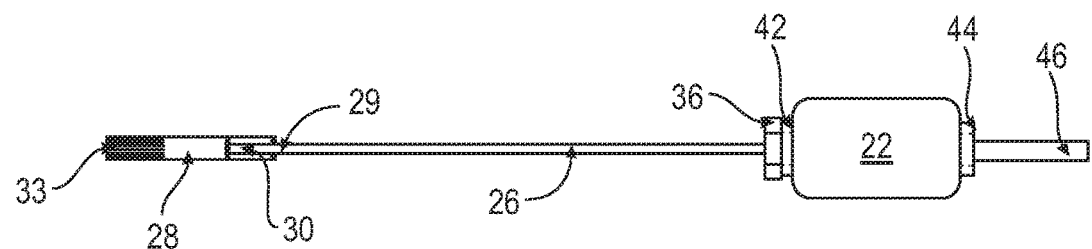
FIG. 6 shows a side view of a needle assembly according to a preferred embodiment wherein the needle assembly comprises a linear needle point array which is used for shading and which is connected to a transducer for vibrating the needle assembly at a second frequency and wherein the transducer is arranged to be connected to an electromagnetic coil drive mechanism.

FIG. 6 shows a needle assembly according to an embodiment. The needle assembly preferably comprises a first end section 29, a middle elongate cylindrical body section 26 and a second end section.

A flat rectangular plate 28 may be mounted to the first end section 29 so that a portion of the needle body is overlapping a flat surface of the rectangular plate 28 and wherein the surface of the needle body is tangential to the flat surface of the rectangular plate 28 where it is joined, seen at 30. The needle body preferably overlaps the rectangular plate 28 by approximately one third of the length of the rectangular plate 28. However, any overlap which results in fixture of the needle body and rectangular plate 28 will be sufficient.

The flat rectangular plate 28 preferably comprises a needle body joining end to which the first end section 29 of the needle body is connected, a central body region and a needle array end section 33. The needle array end section 33 preferably comprises an arrangement of small diameter needles known as sharps.

Each sharp is preferably separated such that the gaps formed may hold ink once the needle array 33 is dipped into an ink source and provide capillary action once the needle array 33 enters the skin of the tattoo subject to introduce the ink into the dermis.

Figure 7:
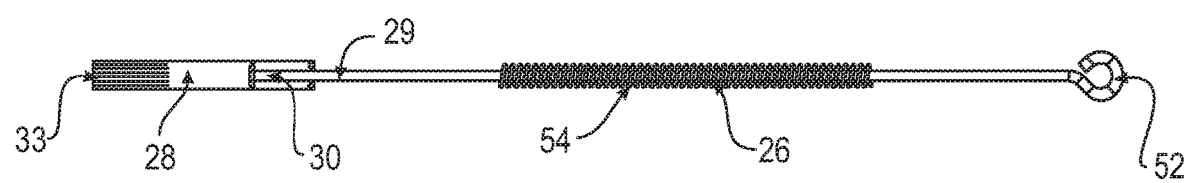
FIG. 7 shows a side view of a needle assembly according to a preferred embodiment wherein the needle assembly has a linear needle point array at one end and wherein the other end of the needle assembly has a loop attachment for attaching the needle assembly to a protruding nipple located on a rotating cam and wherein an electromagnetic coil is provided around a portion of the needle assembly in order to additionally vibrate the needle assembly at a second higher frequency.

FIG. 7 shows an embodiment wherein a needle assembly is provided comprising a linear needle point array 33 at one end and a second end loop attachment 52 at the other end which is configured to connect to a rotary drive mechanism. In this embodiment, the needle body 26 is shown encircled by an electromagnetic coil 54. The electromagnetic coil 54 is preferably arranged to react to a variable electrical stimulus which may be connected to the needle assembly such that the needle is caused to vibrate at a second higher frequency in order to lower the insertion force required to penetrate skin layers.

Figure 8:
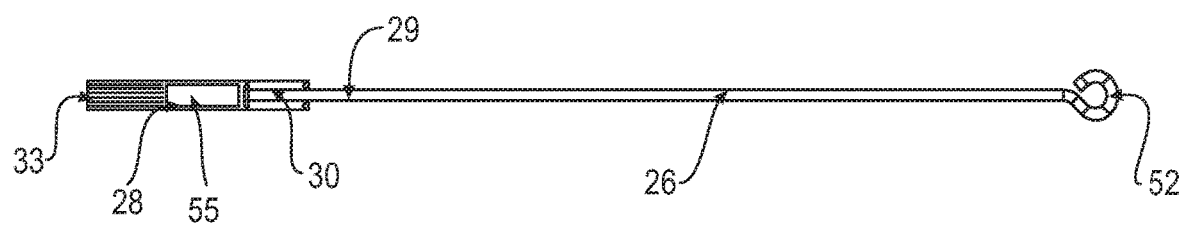
FIG. 8 shows a side view of a needle assembly according to a preferred embodiment wherein one end of the needle assembly has a linear needle point array and the other end of the needle assembly has a loop attachment for attaching the needle assembly to a protruding nipple located on a rotating cam and wherein a pulsatory material such as a piezoelectric plate is attached to the needle assembly.

FIG. 8 shows another embodiment wherein the needle assembly comprises a rectangular needle point array 33 at one end and a second end loop attachment 52 which is configured to connect to a rotary drive mechanism. In this embodiment, the tattooing end of the needle provides a central flat region to which a pulsatory material 55 such as a piezoelectric plate, ceramic or other device may be attached. The pulsatory material 55 may be arranged to react to a variable electrical stimulus which may be connected to the needle assembly such that the needle is caused to vibrate at a second higher frequency.

With reference to FIG. 6, the second end section of the elongate needle body portion may be connected to the flat surface of a hexagonally profiled collar 36 so that the longitudinal axis of the needle body and the collar 36 are coaxial. The hexagonal collar 36 preferably provides a protruding threaded cylinder 37 (see FIG. 9) which originates from the centre point of the outwardly directed face of the collar 36. The threaded cylinder 37 is preferably arranged such that it may be inserted into a corresponding female threaded socket in the transducer housing 22.

The transducer housing 22 may comprise a generally cylindrical hollow component containing a pre-assembled electrical transducer (not shown). The generally cylindrical profile of the transducer housing 22 preferably extends along a central longitudinal axis from a first needle end section 29 to a second end section. The transducer housing 22 is preferably closed at each end by a flat face which is preferably oriented at 90° to the longitudinal axis of the transducer housing 22. At a first end which protrudes from a flat face central to the longitudinal axis of the transducer housing 22 an annular collar 42 may be provided which provides a threaded socket which is preferably arranged to connect or correspond to the threaded cylinder 37.

The other flat face of the transducer housing 22 preferably comprises another annular collar 44 which preferably extends away from a second end flat face of the transducer housing 22 along the central longitudinal axis of the transducer housing 22 so that the second annular collar 44 and transducer housing 22 are also coaxial. The second annular collar 44 preferably comprises an internally threaded socket. The internally threaded socket preferably engages with a cylindrical bar 46. The cylindrical bar 46 may comprise an elongate cylindrical member with a threaded portion at its first end (not visible) and a threaded portion 47 at its second end (as may be seen from FIG. 4). The cylindrical bar 46 preferably has a diameter less than the width of the armature bar 5 of the tattoo device.

According to the preferred embodiment the armature bar 5 is preferably modified to provide a hole at its distal end with a greater diameter than the cylindrical transducer connecting bar 46 such that transducer connecting bar second end threaded portion 47 may pass through the hole in the armature bar 5. This provides a protruding transducer bar second end section to which a nut 50 may be screwed. By screwing the nut 50 against the threaded transducer bar section 47 in the direction of the transducer housing 22, the armature bar 5 will be connected to the transducer housing 22 and consequently, the needle assembly. As the assembly is completed, when armature bar movement is generated by the coil tattoo device, the needle will subsequently move in the required longitudinal direction for tattooing.

As will be described in more detail below with reference to FIG. 11, according to another embodiment a cylindrical bar may extend from the transducer housing 22 second end flat face along the transducer housing central longitudinal axis such that the needle bar central longitudinal axis is coaxial to the transducer housing 22. At the second end of the extended needle bar a loop 52 may be provided which has an inner diameter which preferably corresponds to the rubber nipple 108 provided on the cam of a rotary drive mechanism such that the loop 52 may attach to the rubber nipple 108 to hold the needle in place as lengthwise movement of the needle is generated. The connection means may be used in conjunction with coil, rotary or pneumatic tattoo devices.

The threaded needle end may be inserted into a corresponding threaded socket in the transducer housing 22 by way of a screwing motion, aligning the longitudinal axis of the transducer housing 22 with the longitudinal axis of the needle and pushing the threaded needle end towards the threaded transducer housing socket whilst rotating the threaded needle end in a clockwise manner until fully engaged.

FIG. 9 shows another embodiment wherein a singular point is used as the tattooing end. Where a singular point is used as the tattooing end then flat plate 28 may be omitted.

FIG. 9 shows a needle assembly comprising a singularly pointed first needle end and a second needle end comprising a transducer connecting means 37.

FIG. 10 shows the needle assembly of FIG. 9 with a disengaged transducer housing unit 22.

Figure 11:
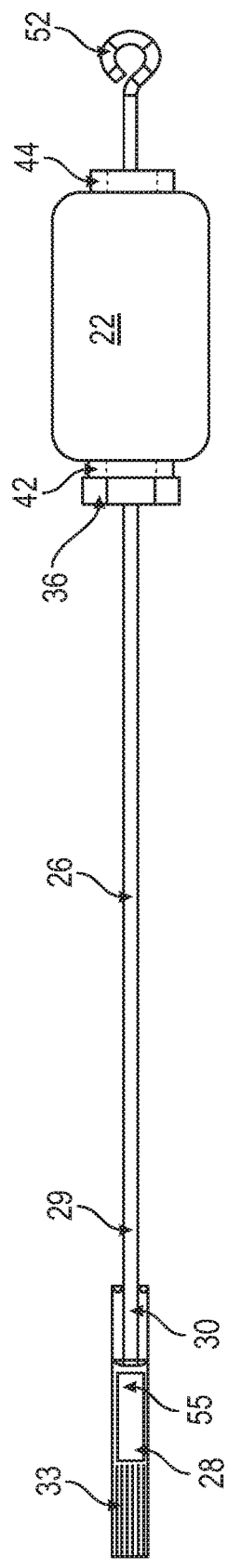
FIG. 11 shows a side view of a needle assembly according to a preferred embodiment with a linear needle point array and loop attachment for attaching to a rotary drive mechanism, wherein a pulsatory material and/or a transducer unit are also attached for vibrating the needle or needle assembly at a second higher frequency.

FIG. 11 shows a needle assembly comprising a rectangular needle point array 33, a second needle end comprising a transducer connecting means, a transducer housing 22 and a transducer end loop attachment 52 configured to connect to a rotary drive mechanism. In this embodiment, the tattooing end of the needle provides a central flat region to which a pulsatory material 55 such as a piezoelectric plate, ceramic or other, may be attached. The pulsatory material 55 may be arranged to react to a variable electrical stimulus which may be connected to the needle assembly such that the needle is caused to vibrate at a second higher frequency in order to lower the insertion force required to penetrate skin layers.

Figure 12:
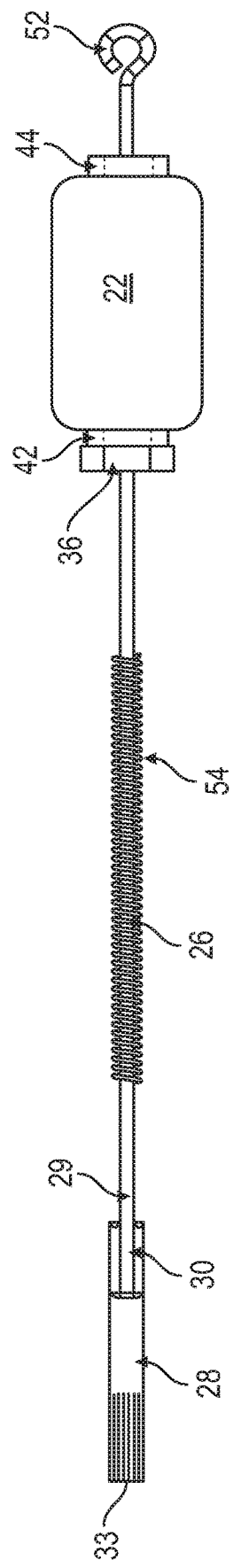
FIG. 12 shows a side view of a needle assembly according to a preferred embodiment with a linear needle point array and loop attachment, wherein an electromagnetic coil and/or a transducer unit are provided for vibrating the needle assembly at a second higher frequency.

FIG. 12 shows a needle assembly comprising a rectangular needle point array 33, a second needle end comprising a transducer connecting means, a transducer housing 22 and a transducer end loop attachment 52 configured to connect to a rotary drive mechanism. In this embodiment the needle body 26 is shown encircled by an electromagnetic coil 54. The electromagnetic coil 54 is preferably arranged to react to a variable electrical stimulus which may be connected to the needle assembly such that the needle is caused to vibrate at a second higher frequency.

Figure 13:
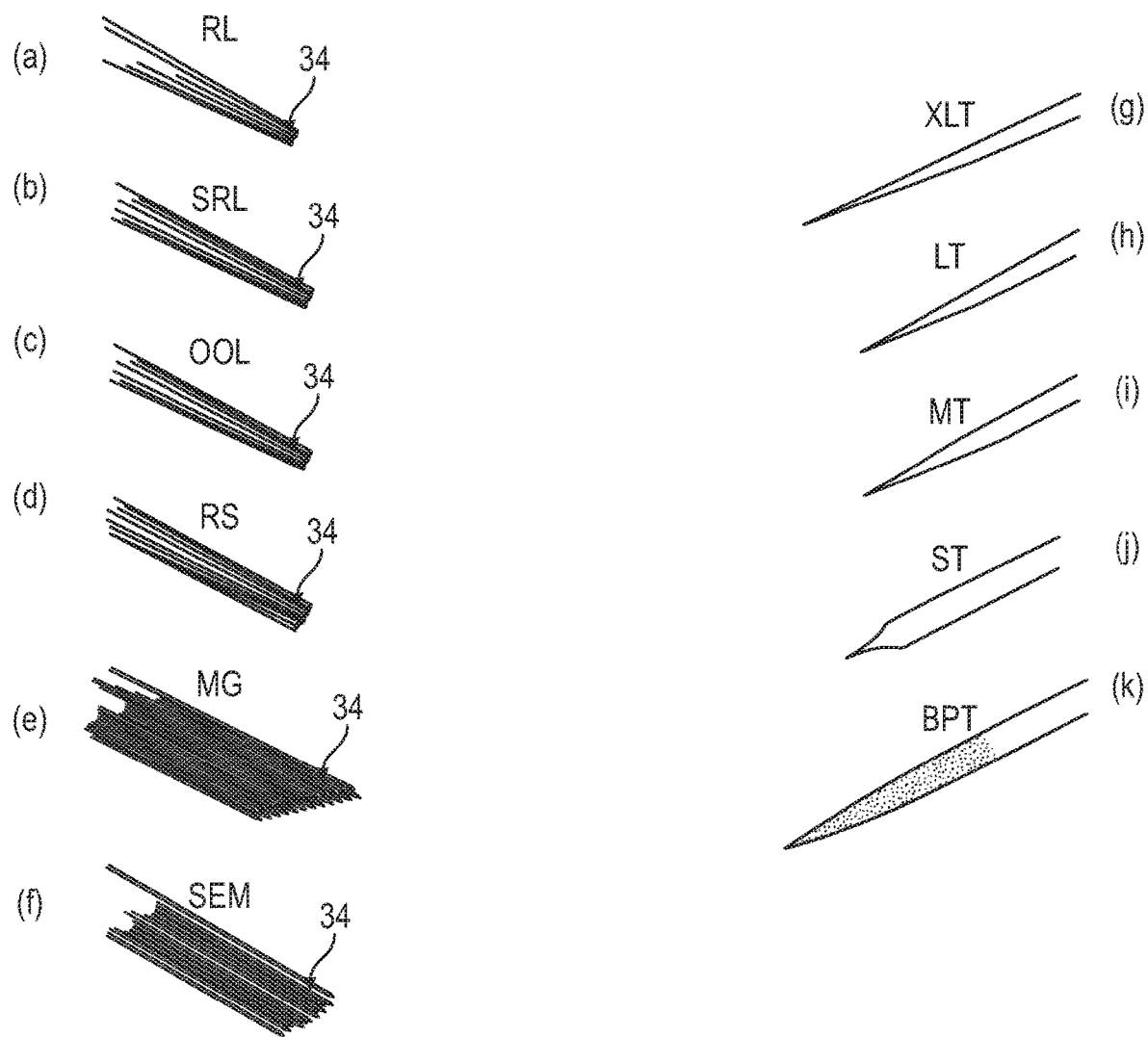
FIG. 13a shows a perspective view of a tattoo needle point wherein sharps extend from a needle bar which is cylindrical to accommodate a circular sharps pattern.
FIG. 13b shows a perspective view of a tattoo needle point wherein sharps extend from a needle bar which is cylindrical to accommodate a circular sharps pattern.
FIG. 13c shows a perspective view of a tattoo needle point wherein sharps extend from a needle bar which is cylindrical to accommodate a circular sharps pattern.
FIG. 13d shows a perspective view of a tattoo needle point wherein sharps extend from a needle bar which is cylindrical to accommodate a circular sharps pattern.
FIG. 13e shows a perspective view of a tattoo needle point wherein sharps extend from a needle bar which is flat in order to accommodate a linear sharps pattern.
FIG. 13f shows a perspective view of a tattoo needle point wherein sharps extend from a needle bar which is flat in order to accommodate a linear sharps pattern.
FIG. 13g shows a perspective view of a tattoo needle point.
FIG. 13h shows a perspective view of a tattoo needle point.
FIG. 13i shows a perspective view of a tattoo needle point.
FIG. 13j shows a perspective view of a tattoo needle point and FIG. 13k shows a perspective view of a tattoo needle point.

The needle array may comprise a variety of commonly used patterns as shown in FIGS. 13*a*-13*k*. The patterns vary in number of needle points and arrangement of needle points to provide different ink coverage of the skin when tattooing. The sharps 34 extend from a needle bar which may be cylindrical to accommodate circular sharps patterns (as shown in FIGS. 13*a* to 13*d*) or flat to accommodate linear sharps patterns (as shown in FIGS. 13*e* and 13*f*). The needle array 33 is permanently connected to the first end of the needle body 29 by a metal weldment such as solder or other permanent metal adhesive.

Any combination of the previously described embodiments, shown and described with reference to FIGS. 6 to 12 may be used as a means of providing a tattoo device with both a first base frequency of vibration and a second higher frequency of vibration such that the operation of performing a tattoo may cause substantially lower levels of pain and result in a better quality of tattoo for a customer.

Where a pulsatory material 55 is used as a second oscillator, there may be one or multiple pieces of the pulsatory material 55 mounted to the needle or needle assembly. It is advantageous to maintain symmetry of the needle or needle assembly. Accordingly, the pulsatory material 55 may be mounted on multiple needle areas in order to avoid non-linear motion of the needle or needle assembly when in use. The pulsatory material 55 may be provided in different shapes or sizes and may be present within the transducer 22 or attached directly to the needle or needle assembly. An amplification structure, such as a horn may be used in conjunction with the needle or needle assembly in order to increase or decrease the amplitude of the vibrations acting on the needle or needle assembly.

Figure 14:
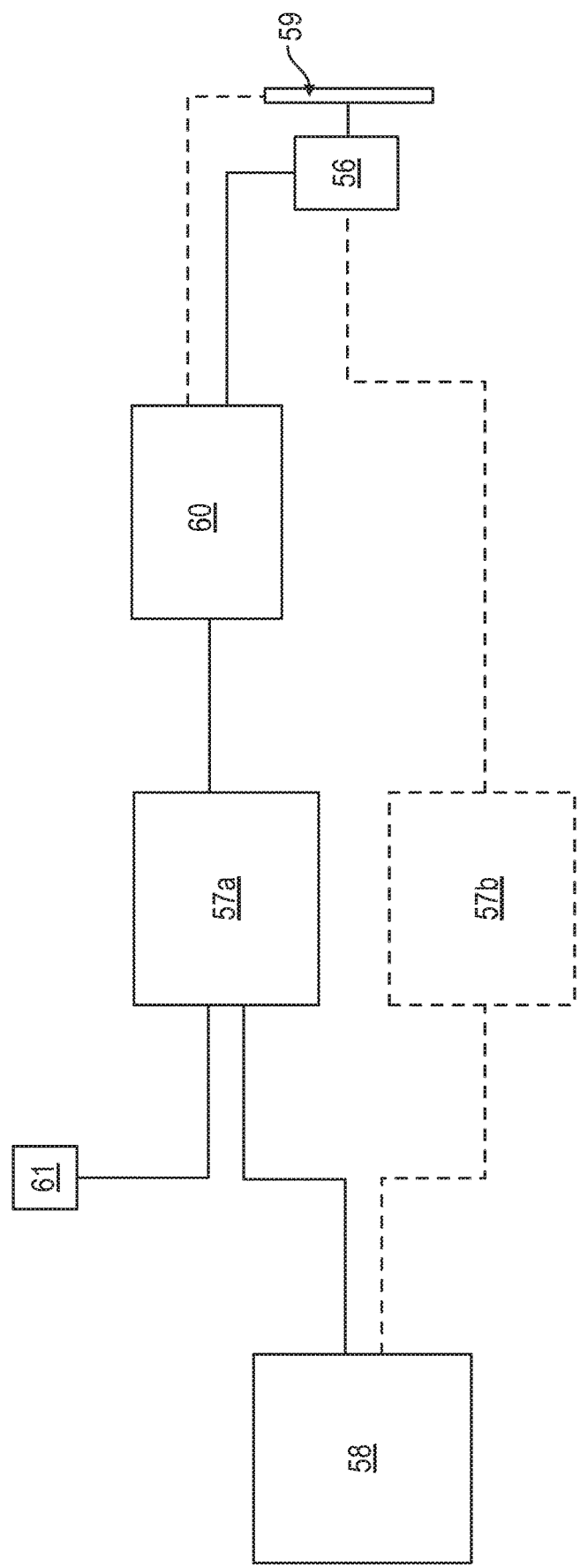
FIG. 14 is a diagram of a possible system layout.

FIG. 14 shows a block diagram of a possible arrangement of a full tattoo system. A tattoo device 60 comprises a transducer 56 connected to a needle 59. The transducer 56 is wired to a power supply 58 via the tattoo device 60 and via an electrical generator unit 57*a*. The electrical generator unit 57*a* is controllable by a user so that the supply voltage may be varied. The generator unit 57*a* may comprise a dedicated adaptable derive electronic control box which is able to track frequency and vibrational amplitude of the needle 59. In varying the supply voltage, the user may adjust the frequency of the needle vibration provided by the transducer 56. This has the effect of lowering entry forces when the needle 59 enters the skin. The trigger of the generator unit 57*a* may be controlled by a foot pedal 61. The user or tattoo artist may engage the foot pedal 61 in order to render the system live. The generator unit 57*a* may be arranged to monitor changes in the transducer drive frequency and electrical impedance and may adapt to the changing conditions in real time.

In another embodiment, the transducer 56 may be wired directly to a generator unit 57*b* and/or the needle 59 may be connected to the tattoo device as shown by the dashed line.

Figure 15:
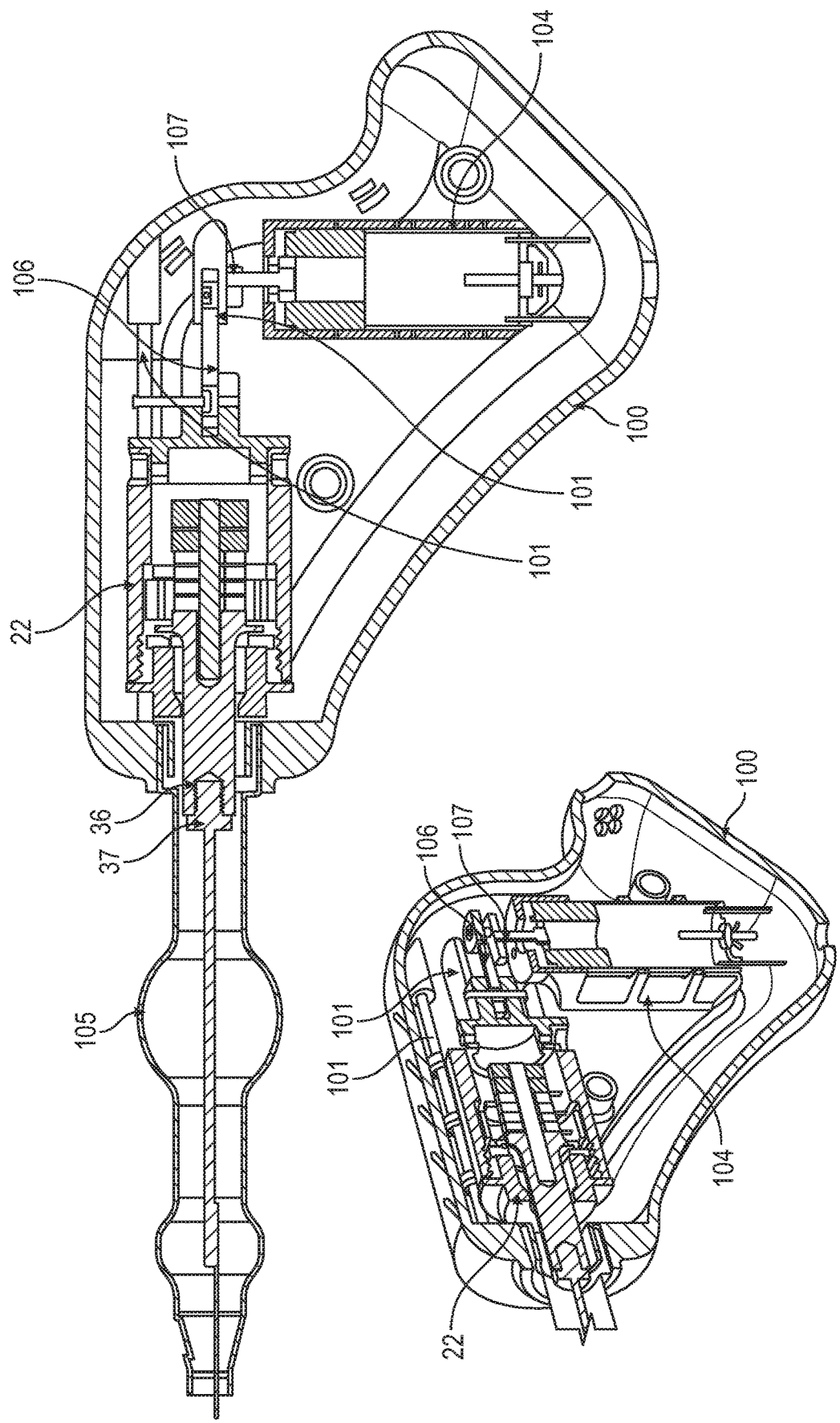
FIG. 15 shows an embodiment of the present invention wherein a tattoo device is provided comprising a handpiece, wherein a transducer within the handpiece reciprocates along internal guide rails.

FIG. 15 shows an embodiment wherein the tattoo device comprises a handpiece 100 having a needle holder 105 attached thereto. The needle holder 105 may be attached to the handpiece 100 by a bayonet fitting. A DC electric motor 104 may be provided within the handpiece 100 and may be arranged to rotate an eccentric cam 107. The cam 107 may be connected to the transducer 22 via a conrod 106. According to this embodiment guide rails 101 are provided such that the housing of the transducer 22 is free to reciprocate along the guide rails 101. The housing of the transducer 22 is preferably connected to the needle or needle assembly such that the needle or needle assembly is vibrated or oscillated at a first frequency determined by the DC electric motor 104. According to the preferred embodiment the needle or needle assembly may be vibrated at a first frequency in the range 1-1000 Hz by the DC electric motor 104. In addition, the needle or needle assembly may also be simultaneously vibrated at a second frequency by a second oscillator (i.e. transducer 22) which is preferably operated at a higher second frequency of, for example, 5-200 kHz. Vibrating the needle or needle assembly at a second higher frequency of 5-200 kHz advantageously lowers the insertion force required to penetrate skin layers and thereby significantly reduces the perception of pain experienced by the subject being tattooed.

Figure 16:
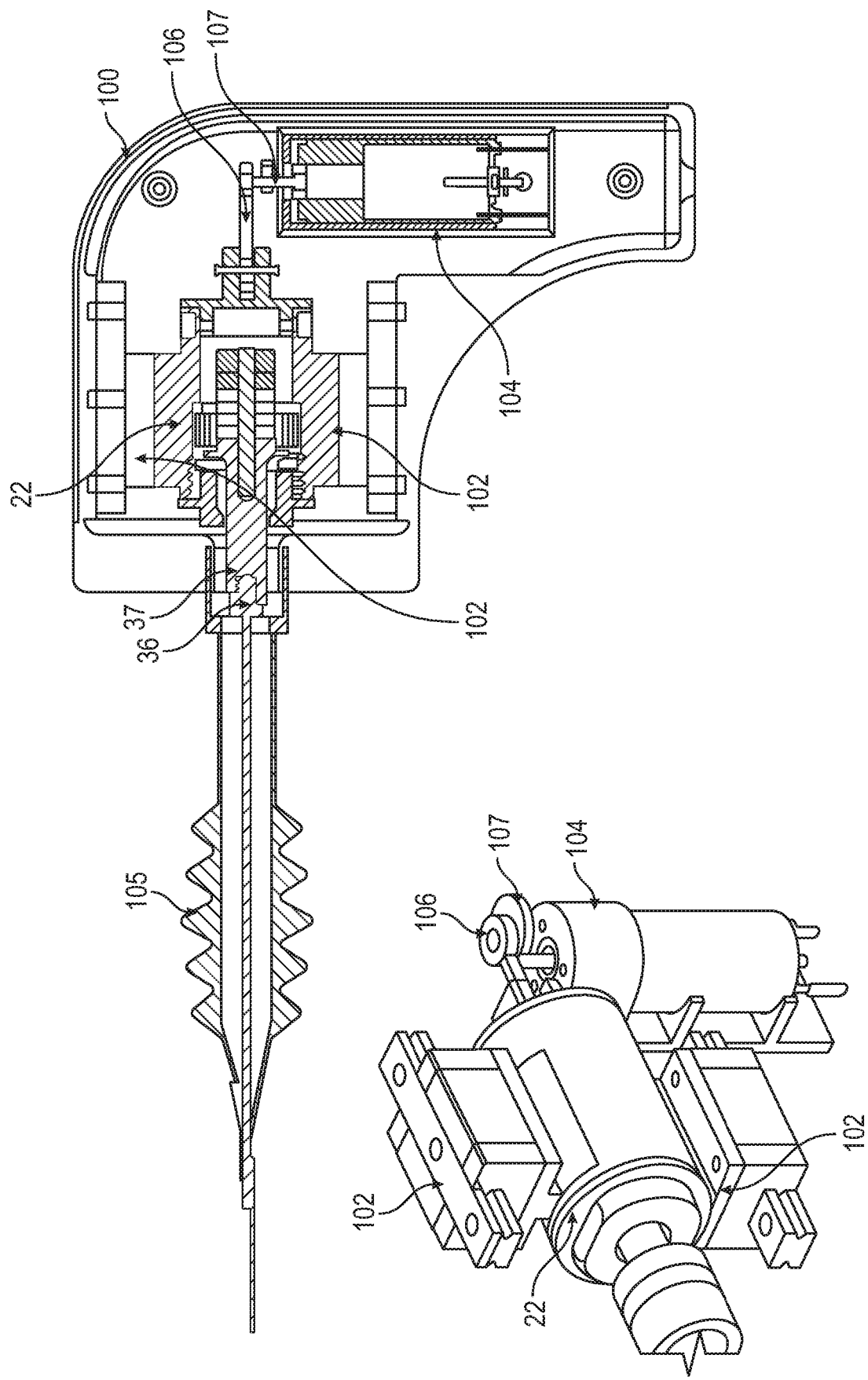
FIG. 16 shows an embodiment of the present invention wherein a tattoo device is provided comprising a handpiece, wherein a transducer within the handpiece reciprocates along linear slides provided within the handpiece.

FIG. 16 shows an embodiment wherein the tattoo device comprises a handpiece 100 having a needle holder 105 attached thereto. The needle holder 105 may be attached to the handpiece 100 by multiple bayonet connections representing different penetration depths. A DC electric motor 104 may be provided within the handpiece 100 and may rotate an eccentric cam 107. The cam 107 may be connected to the transducer 22 via a conrod 106. According to this embodiment linear motion slides 102 are provided such that the housing of the transducer 22 is free to reciprocate along the linear slides 102. The housing of the transducer 22 is preferably connected to the needle or needle assembly such that the needle or needle assembly is vibrated or oscillated at a first frequency determined by the DC electric motor 104. According to the preferred embodiment the needle or needle assembly may be vibrated at a first frequency in the range 1-1000 Hz by the DC electric motor 104. In addition, the needle or needle assembly may also be simultaneously vibrated by a second oscillator (i.e. transducer 22) which is preferably operated at a second higher frequency of, for example, 5-200 kHz. Vibrating the needle or needle assembly at a second higher frequency of 5-200 kHz advantageously lowers the insertion force required to penetrate skin layers and thereby significantly reduces the perception of pain experienced by the subject being tattooed.

Figure 17:
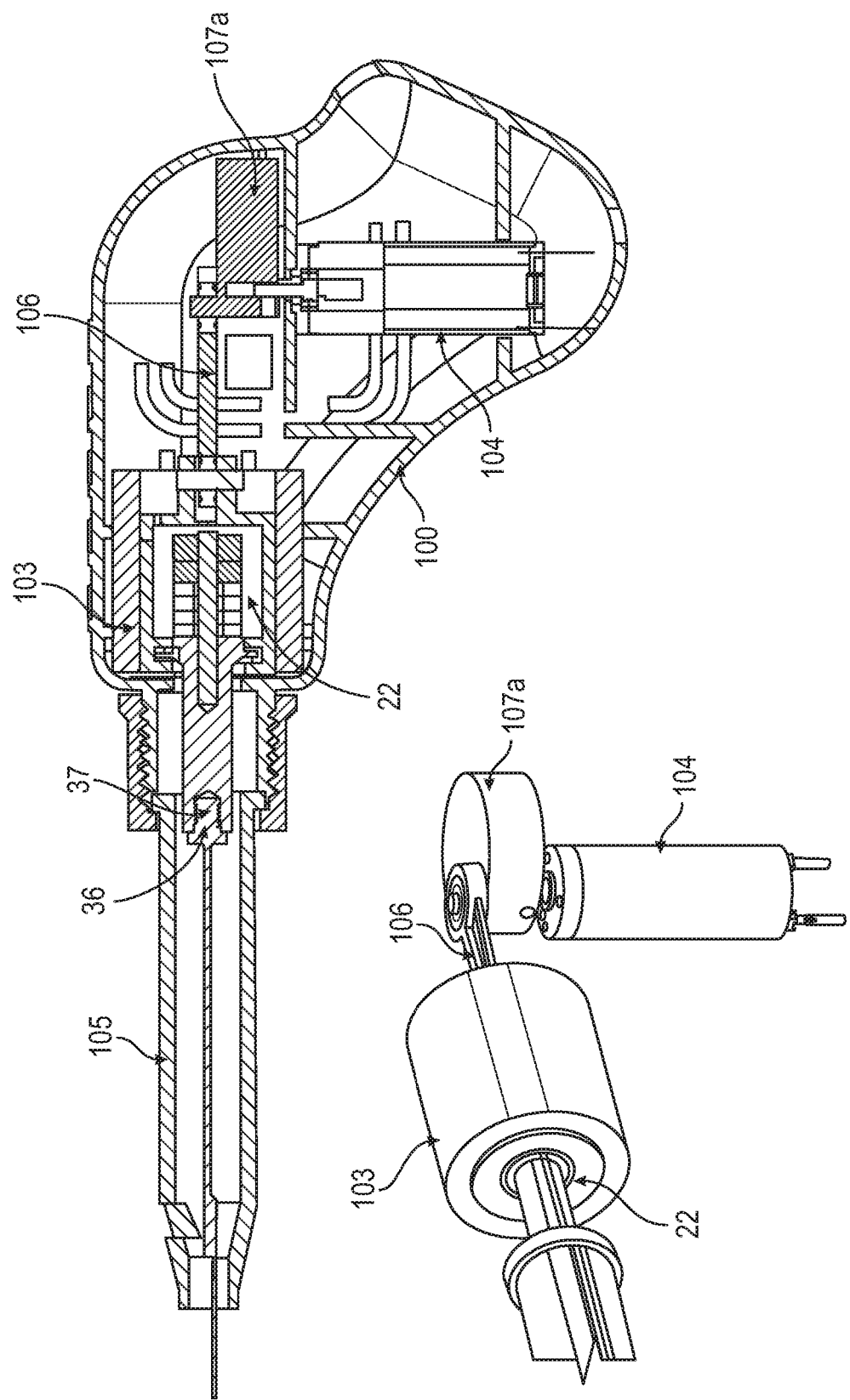
FIG. 17 shows an embodiment of the present invention wherein a tattoo device is provided comprising a handpiece, wherein a transducer within the handpiece reciprocates on a linear motion bearing provided within the handpiece.

FIG. 17 shows an embodiment wherein the tattoo device comprises a handpiece 100 having a needle holder 105 attached thereto. The needle holder 105 may be attached to the handpiece 100 by being clamped using a threaded collet or by being directly screwed into the housing of the handpiece 100. A DC electric motor 104 may be provided within the handpiece 100 and may rotate an eccentric cam 107*a* which preferably has additional mass in order to counter centripetal forces resulting from the weight of the transducer 22. The cam 107*a* with additional mass is preferably connected to the transducer 22 via a conrod 106. According to this embodiment a linear motion bearing 103 is provided such that the housing of the transducer 22 is preferably free to reciprocate along the linear motion bearing 103. The housing of the transducer 22 is preferably connected to the needle assembly such that the needle or needle assembly is vibrated or oscillated at a first frequency determined by the DC electric motor 104. According to the preferred embodiment the needle or needle assembly may be vibrated at a first frequency in the range 1-1000 Hz by the DC electric motor 104. In addition, the needle or needle assembly may also be simultaneously vibrated by a second oscillator (i.e. transducer 22) which is preferably operated at a second higher frequency of, for example, 5-200 kHz. Vibrating the needle or needle assembly at a second higher frequency of 5-200 kHz advantageously lowers the insertion force required to penetrate skin layers and thereby significantly reduces the perception of pain experienced by the subject being tattooed.

Figure 18:
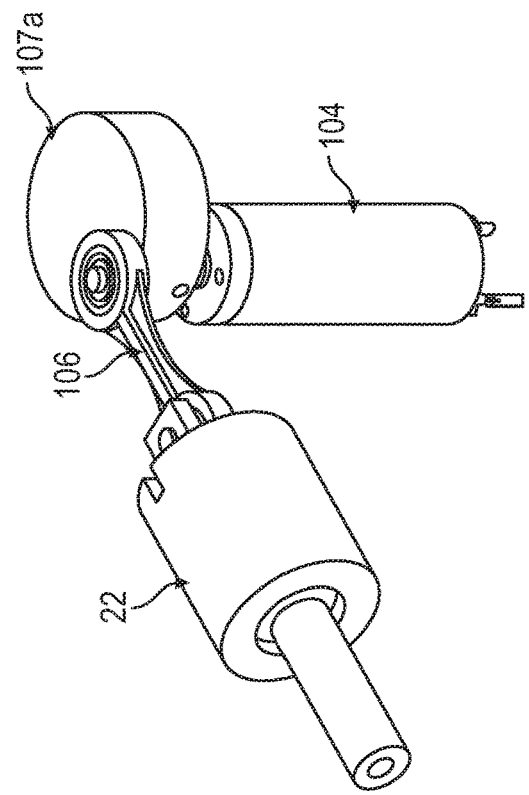
FIG. 18 shows an embodiment of the present invention wherein a cam is provided comprising an eccentric mass which is provided to counteract centripetal forces due to the weight of the transducer.
Figure 18:
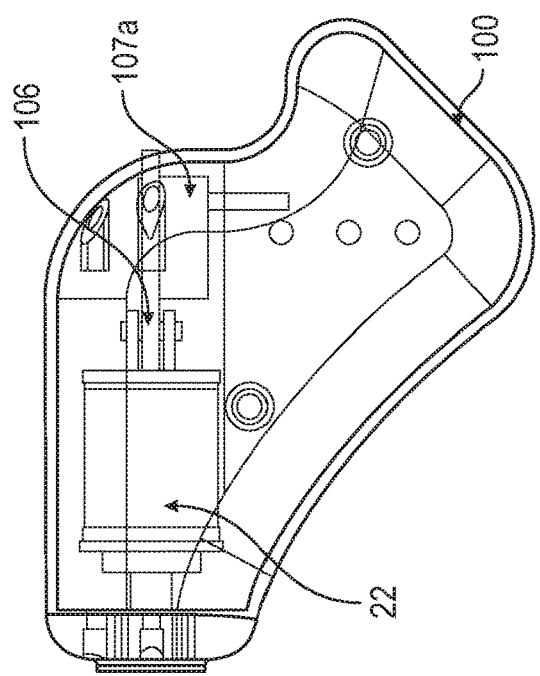

FIG. 18 shows in greater detail an embodiment wherein the cam 107*a* comprises an eccentric mass which is arranged to counteract centripetal forces due to the weight of the transducer 22.

The reciprocating mechanisms as described above according to various embodiment preferably functions such that when the tattoo device is ON, the motor will move the transducer 22 and needle assembly forwards and backwards several times per second. The mass may be approximately 60 grams. The rapid motion of this mass may cause the device to vibrate, making tattooing to any standard slightly problematic. The various described reciprocating mechanisms can substantially alleviate such problems. Also, there is a potential for such vibrations over a sustained period of time to induce Raynauld's phenomenon (known colloquially as white finger). The reciprocating mechanisms provide a balancing force in the opposite direction, effectively cancelling the vibration which may otherwise cause injury to the user after a sustained period of exposure.

Figure 19:
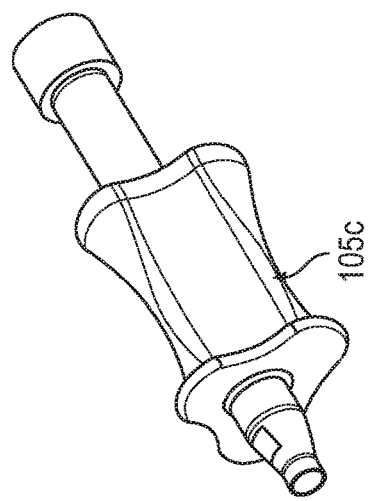
FIG. 19 shows different types of needle holders according to various embodiments.
Figure 19:
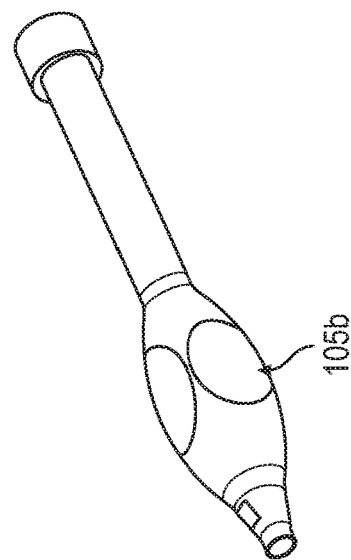
Figure 19:
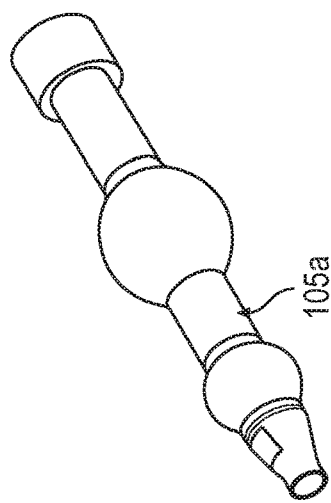

FIG. 19 shows different types of needle holders according to various embodiments. According to an embodiment the needle holder may have a curved grip 105*a*, a faceted grip 105*b* or a triangular grip 105*c*. Other embodiments are contemplated wherein the needle holder may have different shaped grips.

Figure 20:
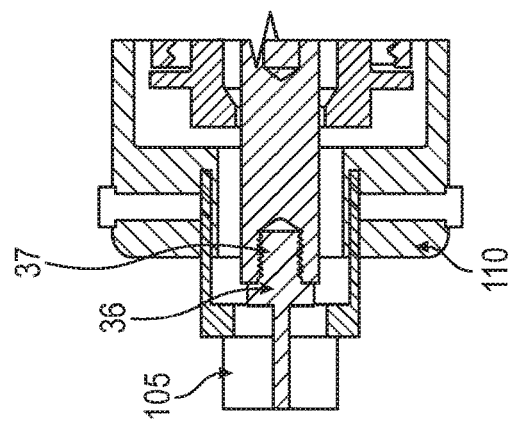
FIG. 20 shows how the needle holder may be attached to a handpiece according to various embodiments.
Figure 20:
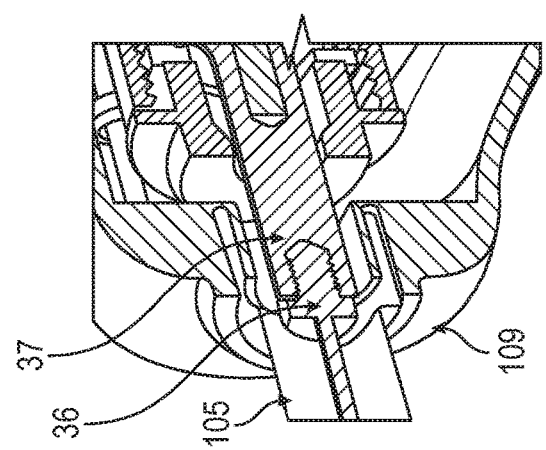
Figure 20:
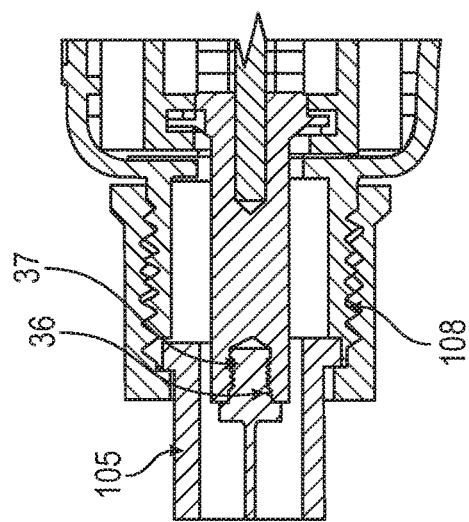

FIG. 20 shows various different attachment mechanisms for attaching the needle holder 105 to the handpiece 100 according to various embodiments. According to an embodiment the needle holder 105 may be clamped using a threaded collet 108 or may be directly screwed to the handpiece 100. According to another embodiment the needle holder 105 may be clamped to the handpiece 100 using a bayonet connection 109. According to a yet further embodiment the needle holder 105 may be attached to the handpiece 100 with one or more grub screws 110 or using a drill chuck.

Figure 21:
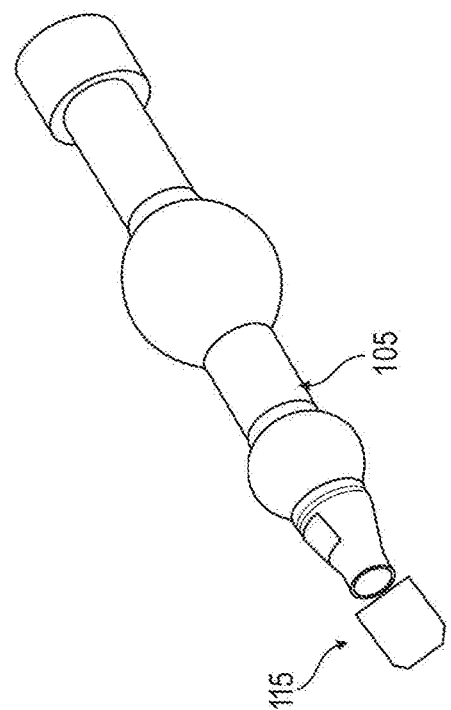
FIG. 21 illustrates different embodiments wherein the needle piercing depth may be adjusted.
Figure 21:
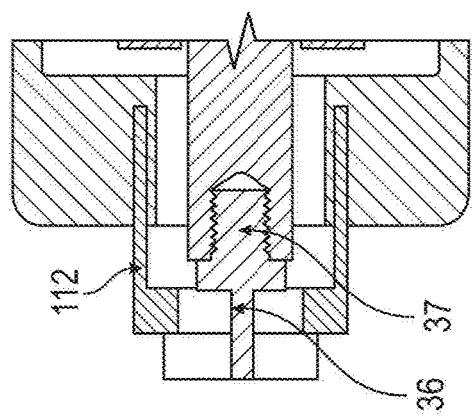
Figure 21:
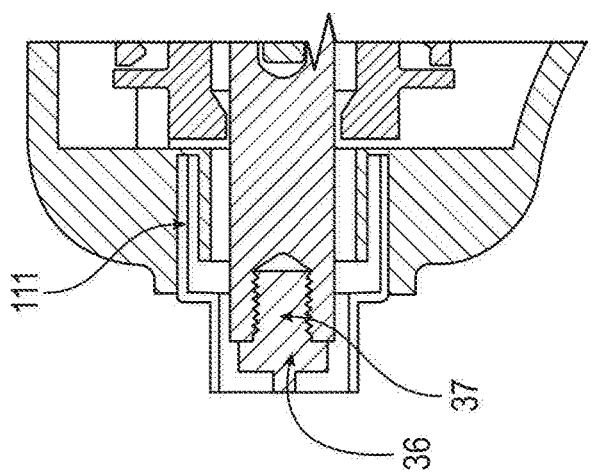

FIG. 21 illustrates further embodiments wherein the needle piercing depth may be adjusted. According to an embodiment a screw threaded needle holder 111 may be provided with graduation markings. According to another embodiment multiple bayonet connections 112 may be provided representing different penetration depths. According to another embodiment an adjustable holder tip 113 may be attached to the needle holder 105.

Figure 22:
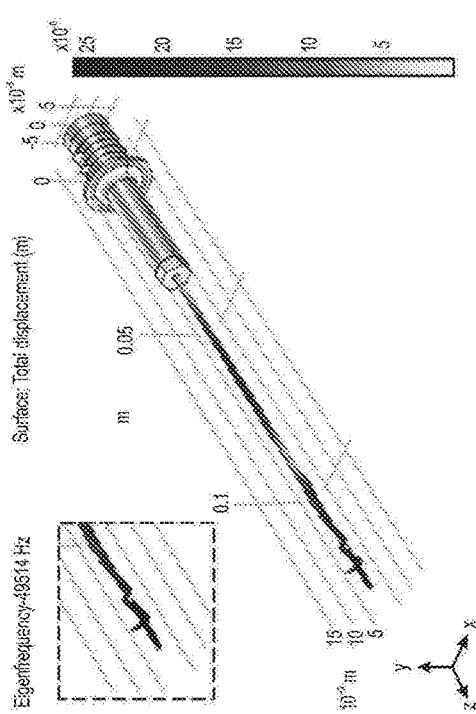
FIG. 22 shows a conventional asymmetric shader needle and a corresponding image of the mode shape which is obtained when the conventional asymmetric needle is vibrated longitudinally and wherein a degree of undesired lateral motion is observed.
Figure 22:
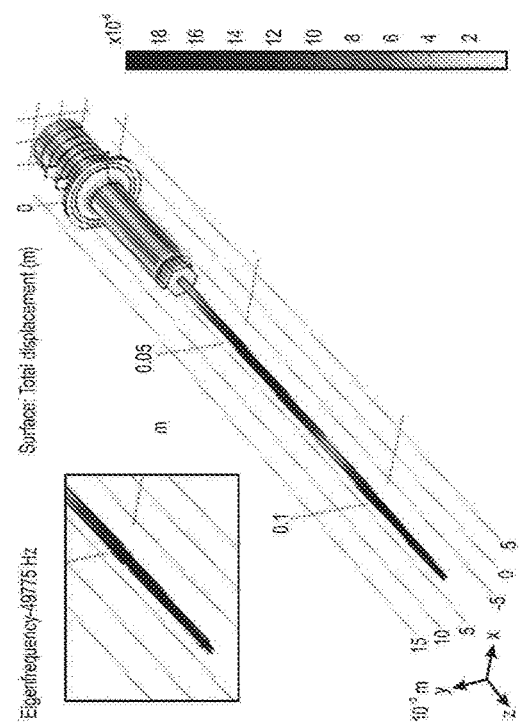
Figure 22:
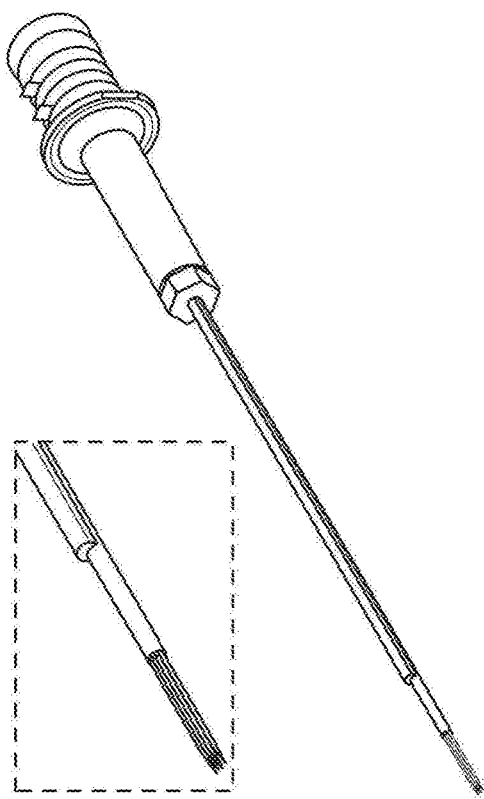

FIG. 22 shows a CAD model of a conventional asymmetric shader needle and a corresponding image of the mode shape which is obtained when the conventional asymmetric needle is vibrated longitudinally and wherein a degree of undesired lateral motion is observed. As will be apparent, the non-symmetry of conventional needles may result in undesirable flexural or lateral motion of the needle when ultrasonic vibration is activated e.g. by a transducer. The undesirable lateral motion of the needle can affect the performance of the tattoo device or tattoo gun. Furthermore, the undesired lateral motion can also reduce the life cycle of conventional needles which may ultimately break if the needle is used for longer periods of time continuously.

Figure 23:
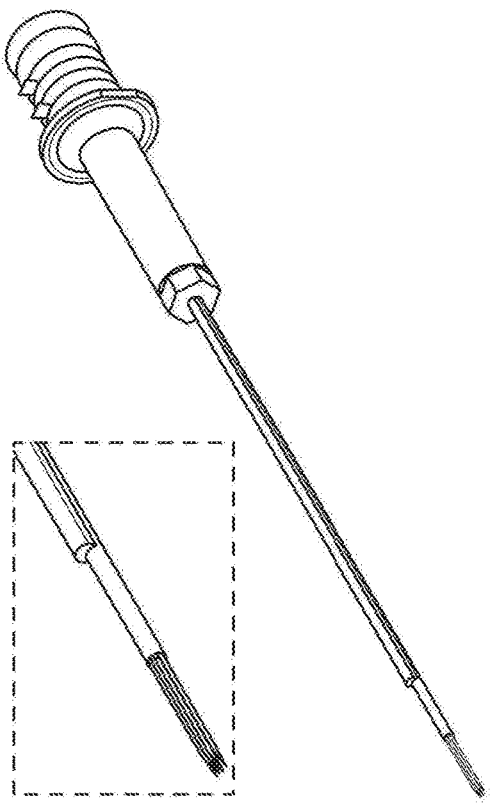
FIG. 23 shows a symmetrical shader needle according to an embodiment of the present invention and a corresponding image of the mode shape which is obtained when the symmetrical needle is vibrated longitudinally wherein no undesired lateral motion is observed.

FIG. 23 shows a CAD model of a symmetrical shader needle according to an embodiment of the present invention and a corresponding image of the mode shape which is obtained when the symmetrical needle is vibrated longitudinally wherein advantageously no undesired lateral motion is observed. Finite Element Modelling and Analysis (FEM/FEA) shows that pure longitudinal motion of the needle is obtained and the problem due to lateral motion of the needle is substantially reduced or completely alleviated.

Figure 24:
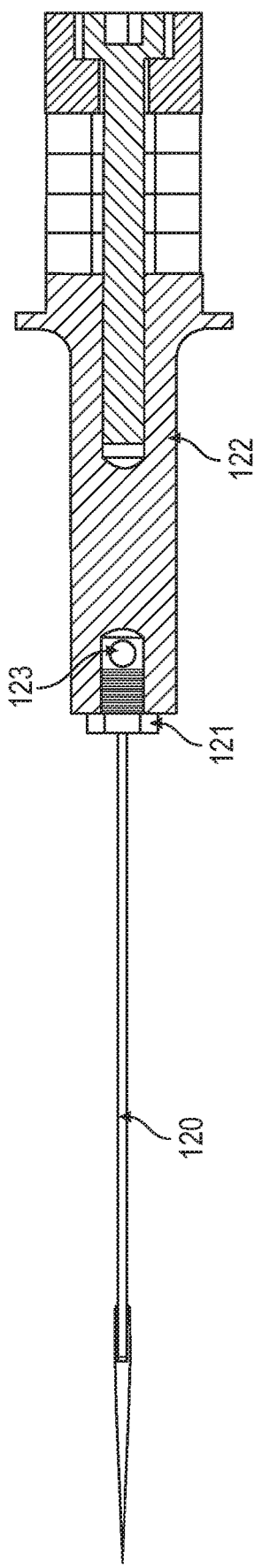
FIG. 24 shows an embodiment wherein a free mass is set in motion by a transducer and impacts a needle causing the needle to move or vibrate without the transducer directly contacting the needle.

FIG. 24 shows an embodiment wherein a free floating mass 123 provided in a chamber which is sealed by a needle boss 121 is set in motion by a transducer 122 and impacts a needle 120 causing the needle to move or vibrate preferably at the same frequency as the transducer 122. As a result the needle 120 is caused to move or vibrate without the transducer 122 directly contacting the needle. According to this embodiment the needle 120 is preferably oscillated by a free mass 123 which is sometimes in contact with the needle 120 and at other times is in contact with the transducer 122. The motion of the free mass 123 is akin to a spherical object in a cylinder being hit on one side by a piston and imparting this energy to the needle at the other end of the cylinder. The effect of the free mass 123 is to increase the vibration amplitude and may allow a reduction in transducer size and/or power to be obtained.

Although the present invention has been described with reference to preferred embodiments, it will be understood by those skilled in the art that various changes in form and detail may be made without departing from the scope of the invention as set forth in the accompanying claims.

The invention claimed is:

1. A tattoo device comprising:
a housing;
a first oscillator which is coupled, in use, to a needle having a sharps end, wherein the first oscillator is arranged and adapted to induce vibrations at a frequency from 1-1000 Hz substantially longitudinally along an axis of the needle in order to cause, in use, the sharps end of the needle to penetrate skin so as to cause punctures therein into which ink can be introduced; and
a second oscillator which is coupled, in use, to the needle;
wherein the second oscillator is arranged and adapted to induce vibrations at a higher frequency than the first oscillator at a frequency from 5-200 kHz in order to lower the insertion force required to penetrate skin layers to cause punctures therein into which ink can be introduced.

2. A tattoo device as claimed in claim 1, wherein the first oscillator operates, in use, at a frequency from 5-250 Hz.

3. A tattoo device as claimed in claim 2, wherein the first oscillator operates, in use, a frequency from 10-150 Hz.

4. A tattoo device as claimed in claim 1, wherein the magnitude of the oscillations produced by the first oscillator is between 0.1 and 10 mm.

5. A tattoo device as claimed in claim 4, wherein the magnitude of the oscillations produced by the first oscillator is between 1-6 mm.

6. A tattoo device as claimed in claim 1, wherein the first oscillator comprises either: (i) a coil or pair of coils; (ii) a rotary oscillator; (iii) a pneumatic oscillator; or (iv) a fluid driven oscillator.

7. A tattoo device as claimed in claim 1, wherein the second oscillator operates, in use, at a frequency between 10-100 kHz or 5-100 kHz.

8. A tattoo device as claimed in claim 7, wherein the second oscillator operates, in use, at a frequency between 20-75 kHz or 25-75 kHz.

9. A tattoo device as claimed in claim 1, wherein the second oscillator comprises an electromagnetic coil in communication with the needle.

10. A tattoo device as claimed in claim 1, wherein the second oscillator comprises a piezoelectric oscillator.

11. A tattoo device as claimed in claim 10, wherein the piezoelectric oscillator comprises either: (i) a single crystal coupled, in use, to a needle: (ii) two or more crystals coupled, in use, to a needle; (iii) one or more ceramic oscillators; or (iv) one or more oscillators comprising lead zirconate titanate ("PZT").

12. A tattoo device as claimed in claim 1, further comprising (i) a horn configured to amplify the oscillations of the second oscillator; and/or (ii) a floating mass located within a chamber positioned between the second oscillator and a needle.

13. A tattoo device as claimed in claim 1, wherein either the first oscillator and/or the second oscillator is arranged and adapted to oscillate at a frequency controlled by an operator.

14. A tattoo device as claimed in claim 1, further comprising a reciprocating device which is arranged and adapted to permit the second oscillator to slide or reciprocate within the housing.

15. A tattoo device as claimed in claim 14, wherein the reciprocating device comprises one or more guide rails, one or more linear slides or one or more linear motion bearings.

16. A tattoo device as claimed in claim 1, comprising a tattoo needle having a sharps end configured to hold ink, cause punctures in skin and introduce the ink into the punctures.

17. A tattoo device as claimed in claim 16, wherein the sharps end of the tattoo needle assembly comprises an array of sharps separated by gaps configured to hold the tattoo ink.

18. A non-therapeutic method of applying a tattoo to a human or an animal comprising:

(i) providing a needle having a sharps end;
(ii) vibrating the needle simultaneously at a first frequency of from 1-1000 Hz with a first oscillator which is coupled, in use, to the needle, wherein the first oscillator is arranged and adapted to induce vibrations at a frequency from 1-1000 Hz substantially longitudinally along an axis of the needle in order to cause, in use, the sharps end of the needle to penetrate skin so as to cause punctures therein into which ink can be introduced and at a second frequency of from 5-200 kHz with a second oscillator which is coupled, in use, to the needle, wherein the second oscillator is arranged and adapted to induce vibrations at a higher frequency than the first oscillator at a frequency from 5-200 kHz in order to lower the insertion force required to penetrate skin layers to cause punctures therein into which ink can be introduced;
(iii) bringing the sharps end of the needle into contact with the skin of a human or an animal so as to cause punctures therein; and
(iv) applying ink to the punctures.

* * * * *